United States Patent [19]

Guillaumet et al.

[11] Patent Number: 5,767,128

[45] Date of Patent: Jun. 16, 1998

[54] 1,3-DIHYDRO-2H-PYRROLO[2,3-B]PYRIDIN-2-ONE COMPOUNDS

[75] Inventors: Gérald Guillaumet, St-Jean-Le-Blanc; Marie-Claude Viaud, Orleans; Laurence Savelon, Saint-Jean-De-Brave, all of France; Panayota Pavli, Athenes, Greece; Pierre Renard, Versailles, France; Bruno Pfeiffer, Eaubonne, France; Daniel-Henri Caignard, Paris, France; Jean-Guy Bizot-Espiard, Paris, France; Gérard Adam, Le Mesnil-Le-Roi, France

[73] Assignee: Adir et Compagnie, Courbevoie, France

[21] Appl. No.: 743,948

[22] Filed: Nov. 5, 1996

Related U.S. Application Data

[62] Division of Ser. No. 497,524, Jul. 3, 1995, Pat. No. 5,618,819.

[30] Foreign Application Priority Data

Jul. 7, 1994 [FR] France .................. 94 08418
Jul. 7, 1994 [FR] France .................. 94 08419

[51] Int. Cl.⁶ .................. C07D 487/02; C07D 471/04; A61K 31/395; A61K 31/52

[52] U.S. Cl. .................. 514/300; 514/421; 514/264; 514/234.2; 514/234.5; 514/228.2; 514/228.5; 514/253; 514/254; 514/278; 514/300; 514/302; 514/299; 544/61; 544/127; 544/362; 546/113; 546/16; 546/116

[58] Field of Search .................. 546/113, 116; 514/300, 302, 421, 264

[56] References Cited

U.S. PATENT DOCUMENTS

| 4,038,396 | 7/1977 | Shen et al. .................. 424/256 |
| 4,866,074 | 9/1989 | Spada et al. .................. 514/300 |
| 5,077,408 | 12/1991 | Guillaumet et al. .................. 545/116 |
| 5,130,311 | 7/1992 | Guillaumet et al. .................. 514/234.2 |
| 5,618,819 | 4/1997 | Guillaumet et al. .................. 514/264 |

*Primary Examiner*—Mukund J. Shah
*Assistant Examiner*—Sabiha N. Qazi
*Attorney, Agent, or Firm*—The Firm of Gordon W. Hueschen

[57] ABSTRACT

The invention relates to a compound selected from those of formula (I):

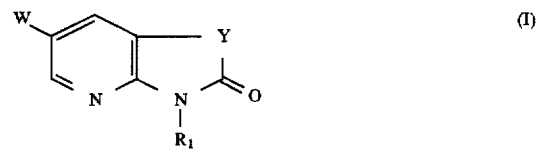

wherein $R_1$, W and Y are as defined in the description, its geometric and/or optical isomers, and its pharmaceutically-acceptable addition salts with an acid or a base useful as analgesies.

7 Claims, No Drawings

1,3-DIHYDRO-2H-PYRROLO[2,3-B]PYRIDIN-2-ONE COMPOUNDS

The present application is a division of our prior-filed application Ser. No. 08/497,524, filed Jul. 3, 1995, now U.S. Pat. No. 5,618,819, issued Apr. 8, 1997.

The present invention relates to new 1,3-dihydro-2H-pyrrolo[2,3-b]pyridin-2-one and oxazolo[4,5-b]pyridin-2(3H)-one compounds, a process for their preparation and pharmaceutical compositions containing them.

Numerous 1,3-dihydro-2H-pyrrolo[2,3-b]pyridin-2-one and oxazolo[4,5-b]pyridin-2(3H)-one compounds are described in therapeutics as having properties such as cardiotonic, insecticidal or anti-inflammatory activities.

Regarding 1,3-dihydro-2H-pyrrolo[2,3-b]pyridin-2-ones, the patent EP-436 333 claims in particular 3-aminocarbonyl-1,3-dihydro-2H-pyrrolo[2,3-b]pyridin-2-ones which are described as having valuable anti-inflammatory properties.

1,3-dihydro-2H-pyrrolo[2,3-b]pyridin-2-ones substituted in the 3-position by alkyls and aryls are also described as anti-inflammatory in an article in the Journal of Medicinal Chemistry (1990), 33, 2697–2706.

Regarding oxazolo[4,5-b]pyridin-2(3H)-ones, and more especially compounds substituted in the pyridine nucleus, the patents EP-357 675 and US-486 674 claim a certain number of compounds which are substituted in the 6-position by pyridines and are described as being cardiotonic.

The compounds of the present invention have a highly original structure in respect of the acyl, hydroxy and/or amino groups substituting them in the pyridine moiety of the heterocycle.

No oxazolo[4,5-b]pyridin-2(3H)-one of that kind is described or claimed in the literature, and the only pyrrolo[2,3-b]pyridin-2-ones substituted in the pyridine nucleus are substituted only by halogens, alkyls or nitrites and are described as being essentially anti-inflammatory.

The new compounds discovered by the Applicant differ from all of the compounds mentioned above by their powerful antalgic properties associated with a virtual absence of anti-inflammatory properties.

The majority of non-morphine analgesic substances known to date also have an anti-inflammatory activity and thus intervene in the processes associated with the symptoms of inflammation (which applies, for example, to salicylated compounds such as aspirin, pyrazole compounds such as phenylbutazone, arylacetic acids or heteroarylacetic acids such as indomethacin . . . ). Being anti-inflammatory agents, those substances inhibit cyclooxygenase, which causes a block in the biosynthesis of numerous chemical mediators (prostaglandins, prostacyclin, thromboxane A2 . . . ). There are therefore many side effects, including the inhibition of platelet aggregation associated with coagulation disorders, and gastrointestinal toxicity with the possibility of ulceration and haemorrhage resulting from a decrease in the biosynthesis of the prostaglandins PGE2 and PGF1a which are cytoprotective towards the gastric mucosa. Apart from the troubles they cause, those side effects may, in many patients who are particularly sensitive to them, render impossible the prescription of antalgic substances that have anti-inflammatory properties.

Since the compounds of the present invention do not interfere with inflammation mediators they do not have the side effects mentioned above.

That characteristic, associated with the absence of toxicity and their high level of activity, makes it possible for the compounds of the present invention to be used as analgesics without the restrictions of use usually applicable to the majority of the products in that class.

The invention relates more specifically to compounds of the general formula (I):

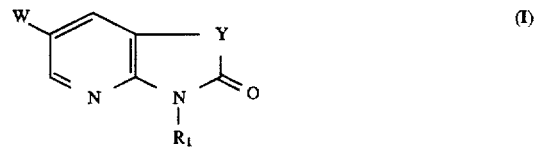

wherein $R_1$ is selected from hydrogen, and alkyl, alkenyl, cyanoalkyl and arylalkyl radicals, W is selected from the groups —A—$R_2$ and

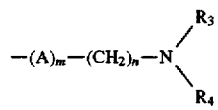

$R_2$ is selected from alkyl, cycloalkyl, cycloalkylalkyl, phenyl, phenylalkyl, naphthyl and naphthylalkyl groups, $R_3$ and $R_4$ are selected, each independently of the other, from hydrogen, and alkyl, phenyl, phenylalkyl, cycloalkyl and cycloalkylalkyl groups, or form together with the nitrogen atom carrying them a heterocyclic system selected from:

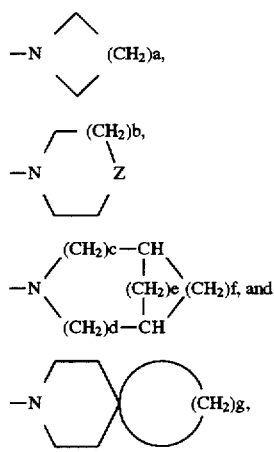

wherein:

a represents an integer of from 0 to 4, b represents 1 or 2, c, d, e and f represent integers of from 0 to 4 g represents 4 or 5,

Z represents O, S or N—$R_7$ wherein $R_7$ represents a hydrogen atom, or an alkyl, phenyl, phenylalkyl, cycloalkyl, cycloalkylalkyl, benzhydryl, naphthyl, pyridyl or pyrimidyl group, n represents an integer of from 1 to 4 inclusive, m represents 0 or 1, A is selected from the group

and the group

Y represents an oxygen atom or a group

wherein $R_5$ and $R_6$ are each selected, independently of the other, from hydrogen, an alkyl radical, a cycloalkyl radical, a cycloalkylalkyl radical, a phenyl radical and a benzyl radical, it being understood in the description of formula (I) that:
the terms "alkyl", "alkenyl" and "alkoxy" denote straight-chain or branched groups having from 1 to 6 carbon atoms which may be unsubstituted or substituted by one or more alkoxy radicals,
the term "aryl" denotes the radicals phenyl, naphthyl or pyridine,
the radicals phenyl, benzyl, phenylalkyl, naphthyl, pyridine, pyrimidyl and benzhydryl may be unsubstituted or substituted by one or more halogen atoms or hydroxy, alkyl, alkoxy, trifluoromethyl or nitro radicals,
the term "cycloalkyl" denotes a ring system having from 3 to 8 carbon atoms,
the terms "cycloalkylalkyl", "arylalkyl", "phenylalkyl" and "naphthylalkyl" denote a cycloalkyl, an aryl, a phenyl or a naphthyl radical bonded by way of a linear or branched carbon chain containing from 1 to 6 carbon atoms,
the heterocyclic system formed by $R_3$ and $R_4$ may be unsubstituted or substituted by one or more halogen atoms or alkyl radicals,
their possible geometric and/or optical isomers, in pure form or in the form of a mixture, and to their pharmaceutically acceptable addition salts with an acid or a base.

The present invention relates also to a process for the preparation of compounds of formula (I) which is characterised in that:

A. when W represents —A—R2, a compound of formula (II):

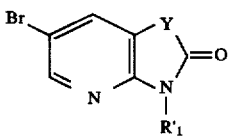

(II)

wherein Y is as defined for formula (I) and $R'_1$ has the same definition as $R_1$ except that $R'_1$ cannot represent a hydrogen atom, is reacted
either in the presence of 1,2-bis(diphenylphosphino)ethane and palladium(II) acetate with an unsaturated ether of formula (III):

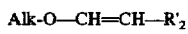

Alk—O—CH=CH—R'2 (III)

wherein Alk represents an alkyl radical having from 1 to 4 carbon atoms and $R'_2$ represents a hydrogen atom or a straight-chain or branched alkyl radical having from 1 to 5 carbon atoms optionally substituted by a phenyl, naphthyl or cycloalkyl group, to obtain a compound of formula (IV):

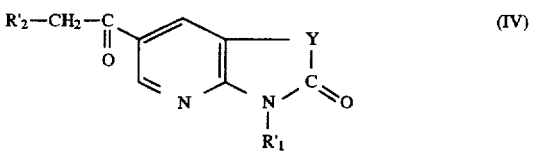

(IV)

wherein $R'_1$, $R'_2$ and Y are as defined above,
or in the presence of tetrakis(triphenylphosphine)palladium and lithium chloride with a compound of formula (V):

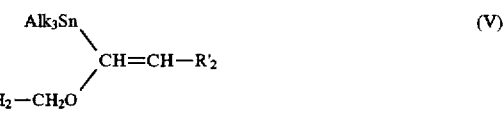

(V)

wherein $R'_2$ and Alk are as defined above, also to yield a compound of formula (IV):

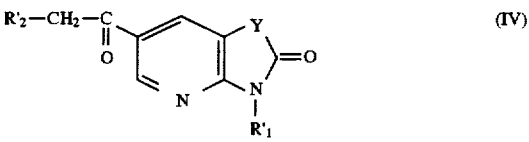

(IV)

or in the presence of zinc with a halogenated compound of formula (VI):

Ar—CH₂—Hal (VI)

wherein Hal represents a halogen atom and Ar represents an optionally substituted phenyl or naphthyl group, to obtain a compound of formula (VII):

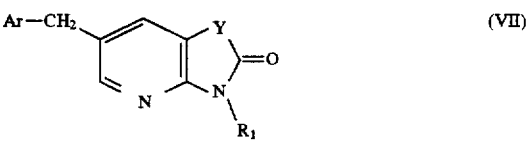

(VII)

wherein Ar is as defined above and $R_1$ is as defined for formula (I),
which is subjected to an oxidation reaction with an oxidizing agent, such as, for example, chromium oxide or N-bromosuccinimide, to yield a compound of formula (VIII):

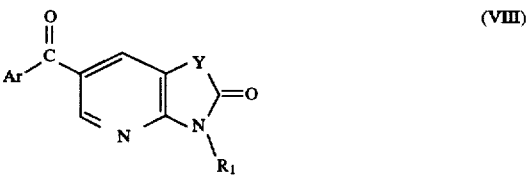

(VIII)

wherein Ar, Y and $R_1$ are as defined above,
it being necessary in the case where N-bromosuccinimide is used and where Y represents the group CH₂ to follow the oxidation reaction by a debromination step with zinc,
it being possible, if desired, for the compounds of formula (IV) and (VII):
to be debenzylated in the presence of palladium-on-carbon and hydrogen, in the case where $R_1$ or $R'_1$ represents a benzyl group, to yield the compounds of formulae (IX) and (X):

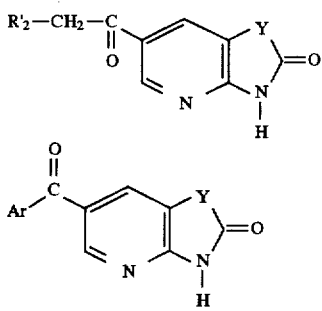

wherein Y, Ar and R'$_2$ are as defined above, to be decyanomethylated in the presence of platinum oxide and hydrogen, in the case where R$_1$ or R'$_1$ represents a cyanomethylated group, to yield those same compounds of formula (IX) and (X), the totality of the compounds (IV), (VIII), (IX) and (X) constituting the compounds of formula (XI):

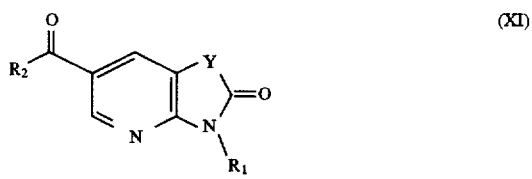

wherein R$_1$, R$_2$ and Y are as defined above, which compounds of formula (XI) may, if desired, be reduced by a reducing agent, such as sodium borohydride, to an alcohol of formula (XII):

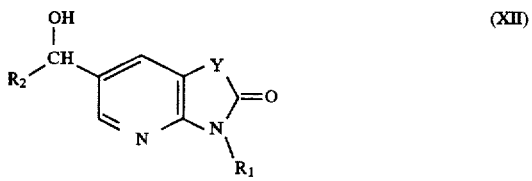

wherein R$_1$, R$_2$ and Y are as defined above,

B. when W represents

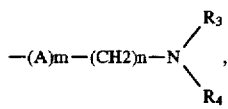

a compound of formula (XIII):

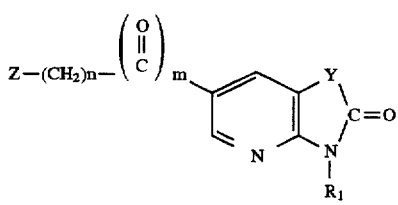

wherein Y, R$_1$, n and m are as defined for formula (I) and Z represents a leaving group, such as a halogen atom or a tosylate group, is reacted with an amine of formula (XIV):

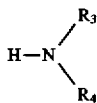

wherein R$_3$ and R$_4$ are as defined for formula (I), to obtain a compound of formula (XV):

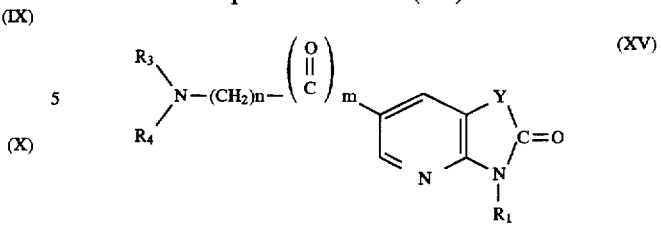

wherein n, m, Y, R$_1$, R$_3$ and R$_4$ are as defined above, the carbonyl function of which may optionally, where m=1, be reduced by a reducing agent, such as, for example, sodium borohydride, to obtain the corresponding alcohol of formula (XVI):

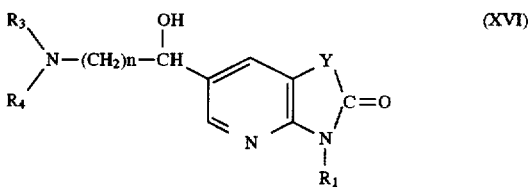

wherein n, Y, R$_1$, R$_2$ and R$_3$ are as defined above, the totality of the compounds of formula (XI), (XII), (XV) and (XVI) forming the compounds of formula (I), which are purified, where appropriate, by a conventional method of purification, are separated, if desired, into their geometric isomers and optical isomers by a conventional method of separation, and are converted, if necessary, into their pharmaceutically acceptable addition salts with an acid or a base.

The pharmacological study of the compounds of the invention has shown that they are of low toxicity, have a high purely analgesic activity and thus do not have the disadvantages inherent in the anti-inflammatory component of the non-morphine compounds having that kind of activity (ulcerogenic action, interference in coagulation processes . . . ).

That pure analgesic activity renders the compounds of the present invention very valuable in a number of indications such as: rheumatic algias, lombosciatic neuralgias, cervicobrachial neuralgias, traumatic algias such as sprains, fractures, luxations, post-traumatic pain, post-operative pain, dental pain, neurological pain such as facial neuralgia, visceral pain such as nephretic colic, dysmenorrhoea, proctological surgery, pain in the ENT region, pancreatitis, various algias, headaches, cancer pain . . . .

The present invention relates also to pharmaceutical compositions containing one of the compounds of formula (I) in the form of a base or converted into a salt with a pharmaceutically acceptable acid, alone or in combination with one or more pharmaceutically acceptable, inert, non-toxic excipients or carriers.

Also included in the invention are pharmaceutical compositions containing one of the compounds of formula (I), in the form of a base or a salt, together with caffeine and in combination with one or more pharmaceutically acceptable, inert, non-toxic excipients or carriers.

Among the pharmaceutical compositions according to the invention there may be mentioned more especially those which are suitable for oral, parenteral, nasal, rectal, perlingual, ocular or respiratory administration and especially injectable preparations, aerosols, eye or nose drops, tablets or dragées, sublingual tablets, sachets, packets, gelatin capsules, glossettes, lozenges, suppositories, creams, ointments, dermal gels etc . . . .

The dosage used varies in accordance with the age and weight of the patient, the administration route, the nature of the therapeutic indication and of possible associated treatments, and ranges from 5 mg to 4 g per 24 hours.

The following Examples illustrate the invention and do not limit it in any way.

PREPARATION 1: 6-BROMO-OXAZOLO[4,5-b]PYRIDIN-2(3H)-ONE

After dissolving oxazolo[4,5-b]pyridin-2(3H)-one (5 g, 23.25 mmol) in N,N-dimethylformamide (100 ml), bromine (1.28 ml, 25.58 mmol) is slowly added. Stirring is maintained at room temperature for 2 hours. Water (50 ml) is then added to the reaction mixture; the title product is isolated after having been filtered, rinsed with a little water and dried in vacuo. The yield obtained is 90%.

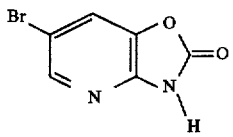

M.p.: 229°–230° C.
IR (KBr): 1750 cm$^{-1}$ (CO carbamate)
$^1$H NMR (CDCl$_3$+D$_2$O), δ(ppm): 7.54 (d, H$_7$, 1H, J$_{5,7}$=2.4 Hz); 8.17 (d, H$_5$, 1H, J$_{5,7}$=2.4 Hz).

PREPARATION 2: 6-BROMO-3-METHYLOXAZOLO[4,5-b]PYRIDIN-2(3H)-ONE 6-bromooxazolo[4,5-b]pyridin-2(3H)-one from Preparation 1 (530 mg, 2 mmol) is dissolved in N,N-dimethylformamide (10 ml), and then sodium hydride (80% in oil) (66 mg, 2.20 mmol) is added thereto. Stirring is maintained at room temperature for 1 hour, and then methyl iodide (426 mg, 3 mmol) diluted with N,N-dimethylformamide (0.5 ml) is added dropwise thereto. The reaction mixture is heated at reflux for 2 hours. When the solution has been cooled and the solvent evaporated off under reduced pressure, the residue is taken up in water and extracted with dichloromethane. The organic phase is dried over magnesium sulfate and filtered, and then the solvent is evaporated off. The title product is purified by chromatography on silica gel (eluant: dichloromethane). The yield obtained is 85%.

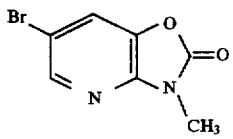

M.p.: 125°–127° C.
IR (KBr): 1770 cm$^{-1}$ (CO carbamate)
$^1$H NMR (CDCl$_3$), δ(ppm): 3.47 (s, NCH$_3$, 3H); 7.52 (d, H$_7$, 1H, J$_{5,7}$=2.2 Hz); 8.16 (d, H$_5$, 1H, J$_{5,7}$=2.2 Hz).

PREPARATION 3: 6-BROMO-3-(CYANOMETHYL)OXAZOLO[4,5-b]PYRIDIN-2(3H)-ONE 6-bromooxazolo[4,5-b]pyridin-2(3H)-one from Preparation 1 (215 mg, 1.0 mmol) is added to a solution of sodium ethanolate prepared with sodium (28 mg, 1.2 mmol) in anhydrous ethanol (6 ml). The reaction mixture is stirred at room temperature for 1 hour, then the ethanol is evaporated off under reduced pressure.

The anion is then dissolved in N,N-dimethylformamide (6 ml), and then bromoacetonitrile (0.1 ml, 1.5 mmol) diluted with a small amount of solvent is added dropwise thereto. The reaction mixture is heated at reflux for 2 hours. When the solution has been cooled and the solvent evaporated off under reduced pressure, the residue is taken up in water and extracted with dichloromethane. The organic phase is dried over magnesium sulfate and filtered, and then the solvent is evaporated off. The title product is purified by chromatography on silica gel (eluant: dichloromethane). The yield obtained is 82%.

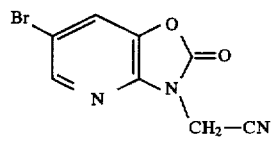

M.p.: 127°–129° C.
IR (KBr): 1780 cm$^{-1}$ (CO carbamate)
$^1$H NMR (CDCl$_3$), δ(ppm): 4.81 (s, NCH$_2$, 2H); 7.66 (d, H$_7$, 1H, J$_{5,7}$=1.5 Hz); 8.28 (d, H$_5$, 1H, J$_{5,7}$=1.5 Hz).

PREPARATION 4: 2-BENZYLOXY)-6-BROMOOXAZOLO[4,5-b]PYRIDINE

The method of operation is the same as that used for the synthesis of the compound of Preparation 2. Benzyl bromide is used instead of methyl iodide. The yield obtained is 60%.

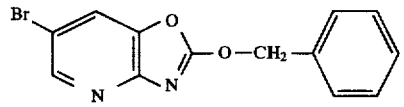

M.p.: 222°–224° C.
IR (KBr): 1740 cm$^{-1}$ (—C=N—)
$^1$H NMR (CDCl$_3$), δ(ppm): 5.40 (s, NCH$_2$, 2H); 7.16 (d, H$_7$, 1H, J$_{5,7}$=1.5 Hz); 7.34 (s, H$_{arom.}$ 5H); 7.42 (d, H$_5$, 1H, J$_{5,7}$=1.5 Hz).

MS (IC/NH$_3$): m/z=307 (M+1)

PREPARATION 5: 6-BROMO-3-(2-PHENYLETHYL)OXAZOLO[4,5-b]PYRIDIN-2(3H)-ONE

Method A:

The title compound is obtained in a yield of 63% by proceeding in the same manner as for the synthesis of the compound of Preparation 2 but replacing the methyl iodide with (2-bromoethyl)benzene.

Method B:

The title compound is obtained in a yield of 78% by proceeding in the same manner as for the synthesis of the compound of Preparation 3 but replacing the bromoacetonitrile with (2-bromoethyl)benzene.

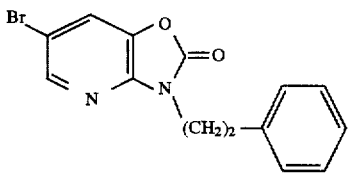

M.p.: 115°–117° C.

IR (KBr): 1780 cm$^{-1}$ (CO carbamate)

$^1$H NMR (CDCl$_3$), δ(ppm): 3.14 (dd, CH$_2$, 2H, J$_1$=8.1 Hz, J$_2$=7.4Hz); 4.15 (dd, NCH$_2$, 2H, J$_1$=8.1 Hz, J$_2$=7.4 Hz); 7.18–7.34 (m, H$_{arom}$, 5H); 7.55 (d, H$_7$, 1H, J$_{5,7}$=2.2 Hz); 8.19 (d, H$_5$, 1H, J$_{5,7}$=2.2 Hz).

PREPARATION 6: 3-ALLYL-6-BROMOOXAZOLO[4,5-b]PYRIDIN-2(3H)-ONE

Method A:

The title compound is obtained in a yield of 41% by proceeding in the same manner as for the synthesis of the compound of Preparation 2 but replacing the methyl iodide with allyl bromide.

Method B:

The title compound is obtained in a yield of 56% by proceeding in the same manner as for the synthesis of the compound of Preparation 3 but replacing the bromoacetonitrile with allyl bromide.

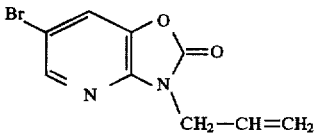

M.p.: 71°–73° C.

IR (KBr): 1785 cm$^{-1}$ (CO carbamate)

$^1$H NMR (CDCl$_3$), δ(ppm): 4.52 (d, NCH$_2$, 2H, J=5.9 Hz); 5.29 (d, H$_{ethyl}$, 1H, J=9.9 Hz); 5.33 (d, H$_{ethyl}$, 1H, J=17.5 Hz); 5.89–6.04 (m, H$_{ethyl}$, 1H); 7.57 (d, H$_7$, 1H, J$_{5,7}$=2.2 Hz); 8.20 (d, H$_5$, 1H, J$_{5,7}$=1.5 Hz).

PREPARATION 7: 6-BROMO-3-(2-CYANOETHYL)OXAZOLO[4,5-b]PYRIDIN-2(3H)-ONE 6-bromooxazolo[4,5-b]pyridin-2(3H)-one (215 mg, 1 mmol) is dissolved in N,N-dimethylformamide (15 ml). Acrylonitrile (64 mg, 1.2 mmol) as well as triethylamine (120 mg, 1.2 mmol) are added in succession to the solution. The reaction mixture is maintained at reflux for 12 hours. When the solution has been cooled and the solvent evaporated off under reduced pressure, the residue is taken up in water and extracted with dichloromethane. The organic phase is dried over magnesium sulfate and filtered, and then the solvent is evaporated off. The title product is purified by chromatography on silica gel (eluant: methylene chloride). The yield obtained is 81%.

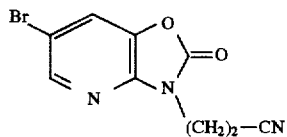

M.p.: 146°–148° C.

IR (KBr): 2240 cm$^{-1}$ (CN), 1785 cm$^{-1}$ (CO carbamate)

$^1$H NMR (CDCl$_3$), δ(ppm): 2.97 (dd, CH$_2$, 2H, J$_1$=7.4 Hz, J$_2$=6.6 Hz); 4.24 (dd, NCH$_2$, 2H, J$_1$=7.4 Hz, J$_2$=6.6 Hz); 7.61 (d, H$_7$, 1H, J$_{5,7}$=1.5 Hz); 8.21 (d, H$_5$, 1H, J$_{5,7}$=1.5 Hz).

PREPARATION 8: 6-BROMO-3-[2-(PYRIDIN-2-YL)ETHYL]OXAZOLO[4,5-b]PYRIDIN-2(3H)-ONE 6-bromooxazolo[4,5-b]pyridin-2(3H)-one (1 g, 4.65 mmol) is suspended in 2-vinylpyridine (5 ml). The solution is heated, with vigorous stirring, until the bromine compound has completely dissolved. Heating at reflux is maintained for 2 hours. When the solution has been cooled, it is taken up in water and extracted with dichloromethane. The organic phase is dried over magnesium sulfate and filtered, and then the solvent is evaporated off. The title product is purified by chromatography on silica gel (eluant: dichloromethane/ethyl acetate: 9/1). The yield obtained is 87%.

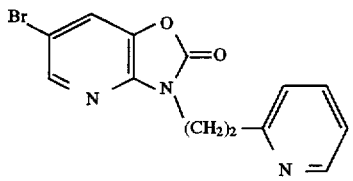

M.p.: 130°–132° C.

IR (KBr): 1780 cm$^{-1}$ (CO carbamate)

$^1$H NMR (CDCl$_3$), δ(ppm): 3.31 (t, CH$_2$, 2H, J=7.4 Hz); 4.34 (t, NCH$_2$, 2H, J=7.4 Hz); 7.08–7.16 (m, H$_{arom}$, 2H); 7.52 (d, H$_7$, 1H, J$_{5,7}$=1.5 Hz); 7.52–7.60 (t, H$_{arom}$, 1H, J=7.4 Hz); 8.15 (d, H$_5$, 1H, J$_{5,7}$=1.5 Hz); 8.50 (d, H$_{arom}$, 1H, J=4.4 Hz).

PREPARATION 9: 6-BROMO-3-[2-(PYRIDIN-4-YL)ETHYL]OXAZOLO[4,5b]PYRIDIN-2(3H)-ONE

The title compound is obtained in a yield of 65% by proceeding in the same manner as for the synthesis of the compound of Preparation 8 but using 4-vinylpyridine instead of 2-vinylpyridine.

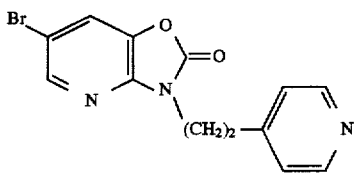

M.p.: 139°–141° C.

IR (KBr): 1780 cm$^{-1}$ (CO carbamate)

$^1$H NMR (CDCl$_3$), δ(ppm): 3.17 (dd, CH$_2$, 2H, J$_1$=8.1 Hz, J$_2$=7.4 Hz); 4.19 (dd, NCH$_2$, 2H, J$_1$=8.1 Hz, J$_2$=7.4 Hz); 7.17 (d, H$_{arom}$, 2H, J=5.9 Hz); 7.55 (d, H$_7$, 1H, J$_{5,7}$=1.5 Hz); 8.16 (d, H$_5$, 1H, J$_{5,7}$=1.5 Hz); 8.51 (d, H$_{arom}$, 2H, J=5.9 Hz).

PREPARATION 10: 1-METHYLPYRROLO[2,3-b]PYRIDINE

Pyrrolo[2,3-b]pyridine (2.00 g, 16.93 mmol) is dissolved in dimethylformamide (15.0 ml) under an argon atmosphere. Sodium hydride (60% in oil) (0.96 g, 40.0 mmol, 1.5 equiv.) is added at 0° C. over a period of 30 minutes. After 30 minutes' stirring at 0° C., iodomethane (1.49 ml, 24.02 mmol, 1.5 equiv.) is added dropwise. After returning to room temperature, the reaction mixture is stirred for 1 hour. The dimethylformamide is evaporated off under reduced pressure, and the product is taken up in water and extracted with dichloromethane. Purification on a silica column (petroleum ether/ethyl acetate 7/3) allows isolation of the title compound in the form of an oil in a yield of 99%.

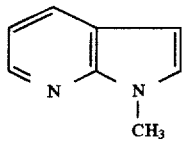

IR (film): 1597 cm$^{-1}$ (C=C, Ar)

$^1$H NMR (CDCl$_3$), δ(ppm): 3.85 (s, 3H, CH$_3$); 6.40 (d, 1H, H$_3$, J$_{3,2}$=3.3 Hz); 7.01 (dd, 1H, H$_5$, J$_{5,4}$=7.4 Hz, J$_{5,6}$=5.2 Hz); 7.13 (d, 1H, H$_2$, J$_{2,3}$=3.3 Hz); 7.85 (d, 1H, H$_4$, J$_{4,5}$=7.4 Hz); 8.29 (d,1H, H$_6$, J$_{6,5}$=5.2 Hz).

PREPARATION 11: 1,3-DIHYDRO-1-METHYL-5-BROMO-2H-PYRROLO[2,3-b]PYRIDIN-2-ONE

Step 1: 1,3-dihydro-3,3,5-tribromo-1-methyl-2H-pyrrolo[2,3-b]pyridin-2-one

Method A:

Pyridinium perbromate (40.58 g, 127.0 mmol, 3.0 equiv.) is added to a solution of the compound of Preparation 10 (5.59 g, 42.3 mmol) in tert-butanol (80 ml). The mixture is stirred at room temperature for 2 hours. The solvents are concentrated by evaporation under reduced pressure, and the crude product is taken up in water and then extracted with ethyl acetate. Evaporation yields 1,3-dihydro-3,3,5-tribromo-1-methyl-2H-pyrrolo[2,3-b]pyridin-2-one in a yield of 93%.

12.46 g (40.7 mmol) of the 1,3-dihydro-3,3,5-tribromo-1-methyl-2H-pyrrolo[2,3-b]pyridin-2-one so obtained are dissolved in 50 ml of dimethylformamide. After the dropwise addition of bromine (4.17 ml, 81.4 mmol, 2 equiv.), the reaction mixture is stirred for 15 hours at room temperature. After evaporation of the solvent under reduced pressure, the product is taken up in water and then extracted with dichloromethane. Once the solvent has been evaporated off, the orange solid is washed with petroleum ether. After drying, the title compound is obtained in a yield of 85%.

Method B:

1-methylpyrrolo[2,3-b]pyridine from Preparation 10 (2.00 g, 15.1 mmol) is dissolved in tert-butanol (132 ml). An equivalent amount of water (132 ml) is slowly added. Bromine (9.28 ml, 128.2 mmol, 12.0 equiv.) is added dropwise using a dropping funnel. After 24 hours' stirring at room temperature, the tert-butanol is removed by evaporation under reduced pressure. The mixture is taken up in a solution of sodium hydrogen carbonate until a neutral pH is reached and is then filtered. Drying gives the title compound in a yield of 91%.

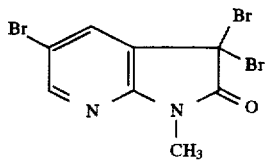

M.p.=210° C.
IR (KBr): ν=1747 cm$^{-1}$ (C=O)
$^1$H NMR (CDCl$_3$), δ(ppm): 3.28 (s, 3H, CH$_3$); 3.55 (s, 2H, CH$_2$); 7.59 (s, 1H, H$_4$); 8.25 (s,1H, H$_6$).

Step 2: 1,3-dihydro-5-bromo-1-methyl-2H-pyrrolo[2,3-b]pyridin-2-one

The compound obtained in Step 1 (0.327 g, 0.85 mmol) is dissolved in acetic acid (8 ml). Zinc (4.3 g, 8.5 mmol, 10 equiv.) is added at room temperature under argon. After 30 minutes' stirring at the same temperature, the reaction mixture is filtered and then subjected to evaporation under reduced pressure. The crude product is extracted with ethyl acetate to a neutral pH and then purified on a silica column (petroleum ether/ethyl acetate 7/3). The title compound is obtained in a yield of 98%.

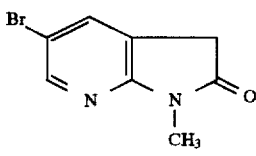

M.p.=149° C.
IR (KBr): ν=1713 cm$^{-1}$ (C=O)
$^1$H NMR (CDCl$_3$), δ(ppm): 3.28 (s, 3H, CH$_3$); 3.55 (s, 2H, CH$_2$); 7.59 (s, 1H, H$_4$); 8.25 (s,1H, H$_6$).

PREPARATION 12: 1,3-DIHYDRO-5-BROMO-3,3-DIMETHYL-2H-PYRROLO[2,3-b]PYRIDIN-2-ONE

Under argon, dissolve 3 g (13.21 mmol) of the compound of Preparation 11 in 40 ml of anhydrous tetrahydrofuran. Cool in an ice-bath and add 793 mg (33.03 mmol) of sodium hydride. After 30 minutes' stirring, slowly add 2.06 ml (4.69 g, 33.03 mmol) of methyl iodide. Slowly allow to come to room temperature over a period of 1 hour. Evaporate off the solvent. Take up the residue in water and extract with dichloromethane. Dry the organic phase over magnesium sulfate.

After purification on a silica column, 2.09 g of the title product are obtained in a yield of 62%.

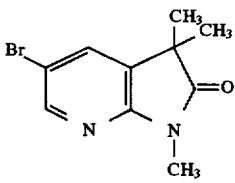

M.p.: 93°–94° C.
$^1$H NMR (CDCl$_3$), δ(ppm) 1.41 (s, 6H, 2×CH$_3$); 3.27 (s, 3H, CH$_3$); 7.50 (d, 1H, H$_4$); 8.23 (d, 1H, H$_6$).

PREPARATION 13: 3-BENZYL-6-BROMOOXAZOLO[4,5-b]PYRIDIN-2(3H-ONE 215 mg (1.0 mmol) of 6-bromooxazolo[4,5-b]pyridin-2(3H)-one are added to a solution of sodium ethanolate prepared from 6 ml of anhydrous ethanol and 28 mg (1.2 mmol) of sodium. After 1 hour's stirring at room temperature, then concentrating to dryness under reduced pressure, the residue is taken up in 6 ml of N,N-dimethylformamide and benzyl bromide is added dropwise. After 2 hours' heating at reflux, cooling and concentrating to dryness under reduced pressure, the residue is taken up in water and extracted with dichloromethane. The crude product obtained by concentrating to dryness is purified by chromatography on a silica column (eluant: dichloromethane).

Yield 68%.

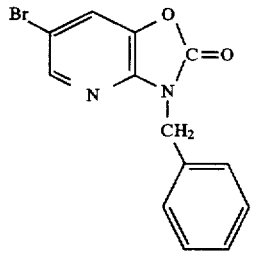

M.p.=78°–80° C.

IR (KBr): 1780 cm$^{-1}$ (CO carbamate)

$^1$H NMR (CDCl$_3$), δ(ppm): 5.12 (s, NCH$_2$, 2H); 7.27–7.39 (m, H$_{arom}$, 3H); 7.47–7.51 (m, H$_{arom}$, 2H); 7.54 (d, H$_7$, 1H, J$_{5,7}$=2.2 Hz); 8.20 (d, H$_5$, 1H, J$_{5,7}$=2.2 Hz).

PREPARATION 14: 6-BROMOMETHYL-3-METHYLOXAZOLO[4,5-b]PYRIDIN-2(3H)-ONE

Step 1: 3,6-dimethyloxazolo[4,5-b]pyridin-2(3H)-one

Method A:

6-bromo-3-methyloxazolo[4,5-b]pyridin-2(3H)-one from Preparation 2 (100 mg; 0.45 mmol) is dissolved in hexamethylphosphoramide (15 ml). Tetramethyltin (0.6 ml, 4.5 mmol) and tetrakis(triphenylphosphine)palladium (500 mg, 0.45 mmol) are added in succession to the solution. Heating at reflux is maintained for 4 hours. The solution is taken up in water and extracted with dichloromethane. The organic phase is dried over magnesium sulfate and filtered, and then the solvent is evaporated off under reduced pressure. 3,6-dimethyl-oxazolo[4,5-b]pyridin-2(3H)-one is purified by chromatography on silica gel (eluant: dichloromethane). The yield obtained is 75%.

Method B:

6-bromo-3-methyloxazolo[4,5-b]pyridin-2(3H)-one from Preparation 2 (414 mg; 1.8 mmol) is dissolved in N,N-dimethylformamide (5 ml). Tetramethyltin (0.3 ml, 2.2 mmol), lithium chloride (229 mg, 5.4 ml) and tetrakis-(triphenylphosphine)palladium (62 mg, 0.1 mmol) are added in succession to the solution. Heating at reflux is maintained for 8 hours. When the solution has been cooled and the solvent evaporated off under reduced pressure, the residue is taken up in water and extracted with dichloromethane. The organic phase is dried over magnesium sulfate and filtered, and then the solvent is evaporated off. 3,6-dimethyl-oxazolo[4,5-b]pyridin-2(3H)-one is purified by chromatography on silica gel (eluant: dichloromethane). The yield obtained is 66%.

Method C:

6-bromo-3-methyloxazolo[4,5-b]pyridin-2(3H)-one from Preparation 2 (414 mg; 1.8 mmol) is dissolved in toluene (10 ml). Tetramethyltin (0.3 ml, 2.2 mmol) and palladium bis (triphenylphosphine)dichloride (70 mg, 0.1 mmol) are added in succession to the solution. Heating at reflux is maintained for 8 hours. When the solution has been cooled and the solvent evaporated off under reduced pressure, the residue is taken up in water and extracted with dichloromethane. The organic phase is dried over magnesium sulfate and filtered, and then the solvent is evaporated off. 3,6-dimethyloxazolo[4,5-b]pyridin-2(3H)-one is purified by chromatography on silica gel (eluant: dichloromethane). The yield obtained is 72%.

M.p.: 114°–116° C.

IR (KBr): 1780 cm$^{-1}$ (CO carbamate)

Step 2: 6-bromomethyl-3-methyloxazolo[4,5-b]pyridin-2 (3H)-one 3,6-dimethyloxazolo[4,5-b]pyridin-2(3H)-one obtained above in Step 1 (0.50 g, 3.05 mmol) is dissolved in distilled carbon tetrachloride (50 ml) and then N-bromosuccinimide (597 mg, 3.35 mmol) and also a catalytic amount of benzoyl peroxide are added thereto. Heating at reflux is maintained for 3 hours. After cooling the solution and then filtering the resulting succinimide, the solvent is evaporated off under reduced pressure. The title product is purified by flash chromatography on silica gel (eluant: dichloromethane). The yield obtained is 83%.

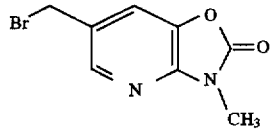

M.p.: 105°–106° C.

IR (KBr): 1785 cm$^{-1}$ (CO carbamate)

$^1$H NMR (CDCl$_3$), δ(ppm): 3.49 (s, NCH$_3$, 3H); 4.53 (s, CH$_2$, 2H); 7.46 (d, H$_7$, 1H, J$_{5,7}$=1.5 Hz); 8.13 (d, H$_5$, 1H, J$_{5,7}$=1.5 Hz).

PREPARATION 15: 3-METHYL-6-[2-(p-TOLUENESULFONYLOXY)ETHYL]OXAZOLO [4,5-b]PYRIDIN-2(3H)-ONE

Step 1: 3-methyl-6-vinyloxazolo[4,5-b]pyridin-2(3H)-one

The protocol of Method C, Step 1 of Preparation 14 is employed, except that the tetramethyltin is replaced with tributylvinyltin. The yield of 3-methyl-6-vinyloxazolo[4,5-b]pyridin-2(3H)-one is 86%.

M.p.: 123°–125° C.

IR (KBr): 1790 cm$^{-1}$ (CO carbamate).

Step 2: 6-(2-hydroxyethyl)-3-methyloxazolo[4,5-b]pyridin-2(3H)-one

A solution of boron hydride (1M in tetrahydrofuran) (5 ml, 5 mmol) is cooled using a salt/ice bath, and then 2,3-dimethyl-1-butene (0.6 ml, 5 mmol) are slowly added. The temperature of the solution is increased to 0° C. and stirring is maintained for a further 2 hours at that temperature. 3-methyl-6-vinyloxazolo[4,5-b]pyridin-2(3H)-one (1.14 mg, 5 mmol) dissolved in tetrahydrofuran (20 ml) is added to the previously prepared solution of thexylborane. The whole is stirred at 0° C. for 2 hours, then a 10% aqueous sodium hydroxide solution (2.40 ml) and also oxygenated water (2.00 ml) are added in succession. After 1 hour's stirring at room temperature and evaporation of the solvent under reduced pressure, the residue is taken up in water. Extraction is carried out with dichloromethane; the organic phase is dried over magnesium sulfate and filtered, and then the solvent is evaporated off under reduced pressure. Purification by flash chromatography on silica gel (eluant: dichloromethane/methanol: 95/5) yields 6-(2-hydroxyethyl) -3-methyloxazolo[4,5-b]pyridin-2(3H)-one in a yield of 78%.

M.p.: 142°–144° C.

IR (KBr): 3400–3100 cm$^{-1}$ (OH), 1775 cm$^{-1}$ (CO carbamate).

Step 3: 3-methyl-6-[2-(p-toluenesulfonyloxy)ethyl]oxazolo[4,5-b]pyridin-2(3H)-one 6-(2-hydroxyethyl)-3-methyloxazolo[4,5-b]pyridin-2(3H)-one obtained in Step 2 (194 mg, 1 mmol) is dissolved in dichloromethane (5 ml). The solution is cooled to 0° C. using a salt/ice bath and then tosyl chloride (286 mg, 1.5 mmol) as well as triethylamine (0.4 ml, 3 mmol) are added. Stirring is maintained for 48 hours while allowing the mixture to return to room temperature. Hydrolysis is carried out by adding water to the reaction mixture, and then extraction is carried out with dichloromethane. The organic phase is dried over magnesium sulfate and filtered, and then the solvent is evaporated off under reduced pressure. The title product is purified by chromatography on silica gel (eluant: dichloromethane). The yield obtained is 81%.

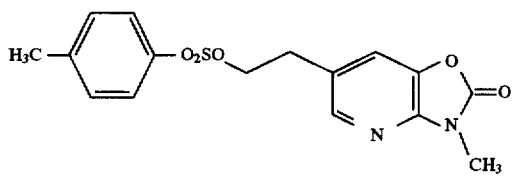

M.p.: 140°–143° C.

IR (KBr): 1790 cm–1 (CO carbamate)

$^1$H NMR (CDCl$_3$), δ(ppm): 2.42 (s, CH$_3$, 3H); 2.97 (t, CH$_2$, 2H, J=6.6 Hz); 3.46 (s, NCH$_3$, 3H); 4.23 (t, CH$_2$, 2H, J=6.6 Hz); 7.13 (d, H$_7$, 1H, J$_{5,7}$=1.5 Hz); 7.27 (d, H$_{arom}$, 2H, J=8.1 Hz); 7.68 (d, H$_{arom}$, 2H, J=8.1 Hz); 7.89 (d, H$_5$, 1H, J$_{5,7}$=1.5 Hz).

PREPARATION 16: 3-METHYL-6-[3-(p-TOLUENESULFONYLOXY)PROPYL]OXAZOLO[4,5-b]PYRIDIN-2(3H)-ONE

Step 1: 3-methyl-6-(prop-2-en-3-al-1-yl)oxazolo[4,5-b]pyridin-2(3H)-one

The method of operation is the same as that used for Step 1, Method C of Preparation 14, 1-tributylstannyl-3,3-diethoxyprop-1-ene and tetrahydrofuran being employed instead of tetramethyltin and toluene, respectively. The reaction mixture is dissolved in water and then a few drops of a 10% hydrochloric acid solution are added and the resulting solution is stirred for 1 hour at room temperature. After extraction with dichloromethane, drying over magnesium sulfate and concentrating to dryness under reduced pressure, the crude product is purified by chromatography on silica gel (eluant: dichloromethane/methanol: 98/2).

Yield: 72%

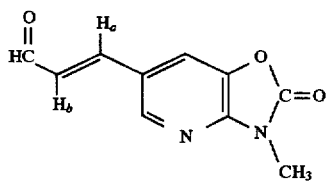

M.p.:210°–212° C.

IR(KBr): 1790 cm$^{-1}$ (CO carbamate), 1680 cm$^{31}$ $^1$ (CO aldehyde)

$^1$H NMR (CDCl$_3$), δ(ppm): 3.51 (s, NCH$_3$, 3H); 6.68 (dd, Hb, 1H, J$_{a,b}$=15.4 Hz, J$_2$=7.4 Hz); 7.49 (d, H$_a$, 1H, J$_{a,b}$=15.4 Hz); 7.60 (d, H$_7$, 1H, J$_{5,7}$=2.2 Hz); 8.29 (d, H$_5$, 1H, J$_{5,7}$=2.2 Hz); 9.72 (d, CHO, 1H, J=7.4 Hz).

Step 2: 3-methyl-6-(3-hydroxyprop-1-yl)oxazolo[4,5-b]pyridin-2(3H)-one 3-methyl-6-(prop-2-en-3-al-1-yl)oxazolopyridin-2(3H)-one (500 mg) is dissolved in 35 cm$^3$ of methanol, then hydrogenated in the presence of 50 mg of palladium-on-carbon. After filtration, the crude product obtained by concentrating to dryness is purified by chromatography on silica gel (eluant: dichloromethane/methanol: 95:5).

Yield: 92%

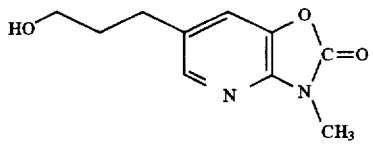

M.p.: 148°–149° C.

IR (KBr): 3400–3100 cm$^{-1}$ (OH), 1770 cm$^{-1}$ (CO carbamate)

$^1$H NMR (CDCl$_3$+D$_2$O), δ(ppm): 1.84–1.94 (m, CH$_2$, 2H); 2.77 (dd, CH$_2$, 2H, J$_1$=8.1 Hz, J$_2$=7.0 Hz); 3.47 (s, NCH$_3$, 3H); 3.70 (dd, CH$_2$, 2H, J$_1$=7.0 Hz, J$_2$5.9 Hz); 7.29 (d, H$_7$, 1H, J$_{5,7}$=1.5 Hz); 7.98 (d, H$_5$, 1H, J$_{5,7}$=1.5 Hz).

Step 3: 3-methyl-6-[3-(p-toluenesulfonyloxy)propyl]oxazolo[4,5-b]pyridin-2(3H)-one The method of operation is the same as that used for the synthesis of the compound of Preparation 15, 3-methyl-6-(3-hydroxypropyl)oxazolo[4,5-b]pyridin-2(3H-one being employed instead of 6-(2-hydroxyethyl)-3-methyloxazolo[4,5-b]pyridin-2(3H)-one. The yield obtained is 78%.

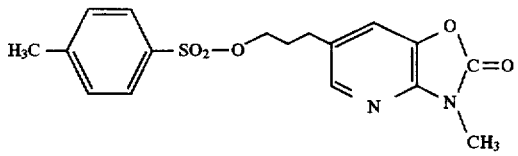

M.p.: 150°–152° C.

IR (KBr): 1790 cm$^{-1}$ (CO carbamate)

$^1$H NMR (CDCl$_3$), δ(ppm): 1.91–2.03 (m, CH$_2$, 2H); 2.47 (s, CH$_3$, 3H); 2.77 (t, CH$_2$, 2H, J=7.4 Hz); 3.46 (s, NCH$_3$, 3H); 4.05 (t, CH$_2$, 2H, J=7.4 Hz); 7.11 (d, H$_7$, 1H, J$_{5,7}$=1.5 Hz); 7.36 (d, H$_{arom}$, 2H, J=8.1 Hz); 7.79 (d, H$_{arom}$, 2H, J=8.1 Hz); 7.88 (d, H$_5$, 1H, J$_{5,7}$=1.5 Hz).

PREPARATION 17: 3-METHYL-6-(BROMOACETYL)OXAZOLO[4,5-b]PYRIDIN-2(3H)-ONE

Method A:

The 3-methyl-6-acetyloxazolo[4,5-b]pyridin-2(3H)-one obtained in Example 1 hereinafter (500 mg, 2.6 mmol) is dissolved in chloroform (15 ml), then bromine (0.2 ml, 2.6 mmol) is added dropwise. The solution is stirred at room temperature for 5 hours. After the solvent has been evaporated off under reduced pressure, the title product is purified by chromatography on silica gel (eluant: dichloromethane). The yield obtained is 73%.

Method B:

The said 3-methyl-6-acetyloxazolo[4,5-b]pyridin-2(3H)-one (500 mg, 2.6 mmol) is dissolved in a 1/1 mixture (15 ml) of ethyl acetate and chloroform, then copper bromide (1.10 g, 4.9 mmol) is added in several portions. The reaction mixture is heated at reflux for 18 hours and then, after cooling, filtration and concentration to dryness, the title product is purified by chromatography on silica gel (eluant: dichloromethane). The yield obtained is 70%.

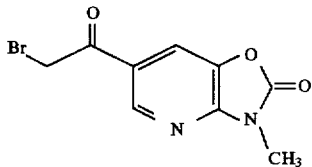

M.p.: 132°–134° C.

IR (KBr): 1770 (CO carbamate), 1670 (CO ketone) cm$^{-1}$ $^1$H NMR (CDCl$_3$), δ(ppm): 3.54 (s, NCH$_3$, 3H); 4.41 (s, CH$_2$, 2H); 7.97 (d, H$_7$, 1H, J$_{5-7}$=1.5 Hz); 8.81 (d, H$_5$, J$_{5-7}$=1.5 Hz).

PREPARATION 18: 1,3-DIHYDRO-5-BROMOMETHYL-1-METHYL-2H-PYRROLO[2,3-b]PYRIDIN-2-ONE

Step 1: 1,3-dihydro-1,5-dimethyl-2H-pyrrolo[2,3-b]pyridin-2-one

The compound of Preparation 11 (0.5 g, 2.2 mmol) and tetramethyltin (0.46 ml, 3.35 mmol, 1.5 equiv.) are dissolved in toluene (35 ml). Tetrakis (triphenylphosphine)palladium (0.077 g, 0.066 mmol, 0.03 equiv.) and lithium chloride (0.28 g, 6.6 mmol, 3 equiv.) are added. The reaction mixture is stirred at reflux, under argon, for 24 hours. After removal of the solvent under reduced pressure, the mixture is hydrolysed with water and extracted with ethyl acetate. Purification on a silica column (petroleum ether/ethyl acetate, 7:3) allows the title compound to be obtained in the form of red crystals in a yield of 49%.

M.p.=98° C.

IR (KBr): ν=1718 cm−1 (C=O)

Step 2: 1,3-dihydro-5-bromomethyl-1-methyl-2H-pyrrolo[2,3-b]pyridin-2-one

Under an argon atmosphere, 1,3-dihydro-1,5-dimethyl-2H-pyrrolo[2,3-b]pyridin-2-one of Step 1 (0.1 g, 0.63 mmol) is dissolved in distilled carbon tetrachloride (12 ml). N-bromosuccinimide (0.12 g, 0.66 mmol, 1.05 equiv.) is added. The reaction mixture is heated at reflux for 4 hours 30 minutes, then, after concentrating to dryness, the crude product is purified on a silica column (petroleum ether/ethyl acetate 8:2).

The title compound is obtained in the form of a crystalline solid in a yield of 84%.

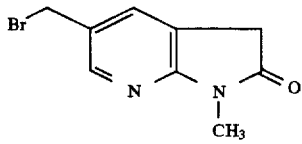

M.p.=65° C.

IR (KBr): ν=1705 cm$^{-1}$ (C=O)

$^1$H NMR (CDCl$_3$), δ(ppm): 3.30 (s, 3H, CH$_3$); 3.56 (s, 2H, CH$_2$), 4.49 (s, 2H, CH$_2$); 7.55 (s, 1H, H-4); 8.19 (s, 1H, H-6).

PREPARATION 19: 1,3-DIHYDRO-5-BROMOACETYL-1-METHYL-2H-PYRROLO[2,3-b]PYRIDIN-2-ONE

Add 170 mg (1.05 mmol) of bromine dissolved in 1 ml of acetic acid dropwise to a solution of 200 mg (1.05 mmol) of 1,3-dihydro-1-methyl-5-acetyl-2H-pyrrolo[2,3-b]pyridin-2-one (obtained as described in Example 13 hereinafter) in 4 ml of acetic acid. After 6 hours' heating at 80° C., the acetic acid is removed under reduced pressure and the residue is taken up in water and then extracted with dichloromethane. The crude product obtained is purified by chromatography on silica gel (eluant ethyl acetate/petroleum ether/dichloromethane, 1/1/1).

Yield: 60%.

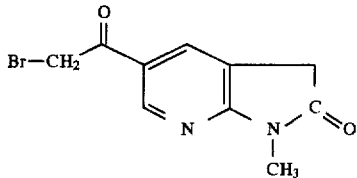

M.p.: 174°–175° C.

$^1$H NMR (CDCl$_3$+D$_2$O), δ(ppm): 3.36 (s, 3H, N—CH$_3$); 3.62 (s, 2H, CH$_2$—C=O); 4.38 (s, 2H, CH$_2$Br); 8.07 (s, 1H, H$_4$); 8.88 (s, 1H, H$_6$).

PREPARATION 20: 3-METHYL-6-(2-BROMO-1-HYDROXYETHYL)OXAZOLO[4,5-b]PYRIDIN-2(3H)-ONE 3-methyl-6-bromoacetyloxazolo[4,5-b]pyridin-2(3H)-one (1 mmol) obtained in Preparation 17 is dissolved in 15 ml of anhydrous methanol, then sodium borohydride (42 mg, 1.1 mmol) is added. The reaction mixture is stirred for 5 hours at room temperature and then hydrolysed. 3-methyl-6-(2-bromo-1-hydroxyethyl) oxazolo[4,5-b]pyridin-2(3H)-one is isolated by filtration and then dried in vacuo.

Yield: 70%.

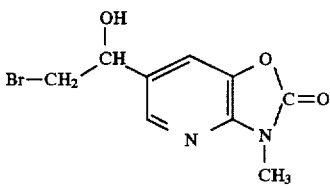

M.p.: 127°–129° C.

IR (KBr): 3400–3100 cm$^{-1}$ (OH), 1770 cm$^{-1}$ (CO carbamate)

$^1$H NMR (CDCl$_3$+D$_2$O), δ(ppm): 3.48 (s, NCH$_3$, 3H); 3.54 (dd, CHBr, 1H, J$_1$=10.5 Hz, J$_2$=8.1 Hz); 3.63 (dd, CHBr, 1H, J$_1$=10.5 Hz, J$_2$=3.7 Hz); 5.00 (dd, CHOH, 1H, J$_1$=8.1 Hz, J$_2$=3.7 Hz); 7.51 (d, H$_7$, 1H, J$_{5,7}$=1.5 Hz); 8.16 (d, H$_5$, 1H, J$_{5,7}$=1.5 Hz).

PREPARATION 21: 3-BENZYL-6-BROMOACETYLOXAZOLO[4,5-b]PYRIDIN-2(3H)-ONE

The procedure is as for Preparation 17, but with the replacement of 3-methyl-6-bromooxazolo[4,5-b]pyridin-2(3H)-one with 3-benzyl-6-bromooxazolo[4,5-b]pyridin-2(3H)-one obtained in Preparation 13.

PREPARATION 22: 3-ETHYL-6-BROMOMETHYLOXAZOLO[4,5-b]PYRIDIN-2(31H)-ONE

The procedure is as for Preparations 2 and 14, but with the replacement of methyl iodide with ethyl iodide in the alkylation step.

PREPARATION 23: 1,3-DIHYDRO-5-BROMOACETYL-1,3,3-TRIMETHYL-2H-PYRROLO[2,3-b]PYRIDIN-2-ONE

By proceeding as for Preparation 19, but replacing 1,3-dihydro-1-methyl-5-acetyl-2H-pyrrolo[2,3-b]pyridin-2-one with 1,3-dihydro-5-acetyl-1,3,3-trimethyl-2H-pyrrolo[2,3-b]pyridin-2-one (Example 12 hereinafter). 1,3-dihydro-5-bromoacetyl-1,3,3-trimethyl-2H-pyrrolo[2,3-b]pyridin-2-one is obtained in a yield of 59%.

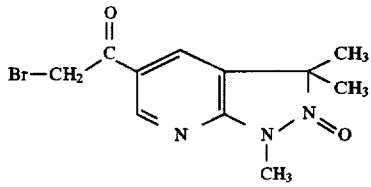

M.p.=185°–186° C.

¹H NMR (CDCl₃): δ(ppm): 1.46 (s, 6H, 2×CH₃); 3.22 (s, 3H, N—CH₃); 4.38 (s, 2H, CH₂—Br); 8.00 (s,1H, H₄); 8.85 (s,1H, H₆).

EXAMPLE 1

3-METHYL-6-ACETYLOXAZOLO[4,5-b]PYRIDIN-2(3H)-ONE

Method A: Coupling with butyl vinyl ether 6-bromo-3-methyloxazolo[4,5-b]pyridin-2(3H)-one from Preparation 2 (0.50 g, 2.18 mmol) is dissolved in N,N-dimethylformamide (5 ml). Triethylamine (0.44 g, 4.36 mmol), butyl vinyl ether (1.2 g, 12 mmol), 1,2-bis(diphenylphosphino)ethane (24 mg, 0.06 mmol) and palladium(II) acetate (12 mg, 0.054 mmol) are then added in order. The solution is heated at reflux for 8 hours under an inert atmosphere. When it has been cooled, the solution is hydrolysed with a 10% hydrochloric acid solution and stirring is maintained for 1 hour. N,N-dimethylformamide is evaporated off under reduced pressure and then the residue is taken up in water and extracted with dichloromethane; the organic phase is then dried over magnesium sulfate and filtered, and the solvent is subsequently evaporated off. The title product is purified by flash chromatography on silica gel (eluant: dichloromethane/ethyl acetate: 8/2). The yield obtained is 90%.

Method B: Coupling with 1-ethoxy-1-(trimethylstannyl)ethylene 6-bromo-3-methyloxazolo[4,5-b]pyridin-2(3H)-one from Preparation 2 (700 mg, 3.05 mmol) is dissolved in tetrahydrofuran (20 ml) and then (3.14 mmol, 0.59 ml) of 1-ethoxy-1-(trimethylstannyl)ethylene is introduced. Tetrakis (triphenylphosphine) palladium (180 mg, 0.15 mmol) and lithium chloride (380 mg, 8.84 mmol) are then added in order. The solution is heated at reflux for 8 hours under an inert atmosphere. When it has been cooled, the solution is hydrolysed with a 10% hydrochloric acid solution and stirring is maintained for 1 hour. The tetrahydrofuran is evaporated off under reduced pressure and then the residue is taken up in water and extracted with dichloromethane; the organic phase is then dried over magnesium sulfate and filtered, and the solvent is subsequently evaporated off. The title product is purified by flash chromatography on silica gel (eluant: dichloromethane/ethyl acetate: 8/2). The yield obtained is 60%.

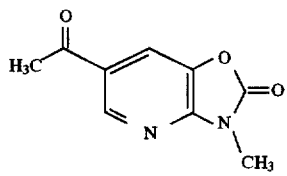

M.p.: 162°–164° C. (i-PrOH)

IR (KBr): 1790 cm⁻¹ (CO carbamate), 1670 cm⁻¹ (CO ketone)

¹H NMR (CDCl₃), δ(ppm): 2.53 (s, CH₃, 3H); 3.63 (s, NCH₃, 3H); 7.91 (d, H₇, 1H, J₅₋₇=1.5 Hz); 8.72 (d, H₅, 1H, J₅₋₇=1.5 Hz).

EXAMPLE 2

3-BENZYL-6-ACETYLOXAZOLO[4,5-b]PYRIDIN-2(3H)-ONE

The method of operation is the same as that used for the synthesis of the compound of Example 1 (coupling with 1-ethoxy-1-(trimethylstannyl)ethylene). 6-bromo-3-benzyloxazolo[4,5-b]pyridin-2(3H)-one from Preparation 13 being used instead of 6-bromo-3-methyloxazolo[4,5-b]pyridin-2(3H)-one. The yield obtained is 75%.

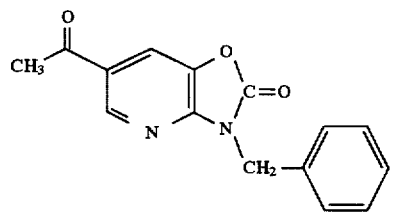

M.p.=163°–164° C.

IR (KBr): 1780 cm⁻¹ (CO carbamate), 1670 cm⁻¹ (CO ketone)

¹H NMR (CDCl₃), δ(ppm): 2.62 (s, CH₃, 3H); 5.12 (s, NCH₂, 2H); 7.27–7.78 (m, H_{arom}, 3H); 7.49–7.55 (m, H_{arom}, 2H); 7.93 (d, H₇, 1H, J₅₋₇=1.5 Hz); 8.77 (d, H₅, 1H, J₅₋₇=1.5 Hz).

EXAMPLE 3

3-CYANOMETHYL-6-ACETYLOXAZOLO[4,5-b]PYRIDIN-2(3H)-ONE

The method of operation is the same as that used for the synthesis of the compound of Example 1 (coupling with 1-ethoxy-1-(trimethylstannyl)ethylene). 6-bromo-3-(cyanomethyl)oxazolo[4,5-b]pyridin-2(3H)-one from Preparation 3 is used instead of the 6-bromo-3-methyloxazolo[4,5-b]pyridin-2(3H)-one from Preparation 2. The yield obtained is 60%.

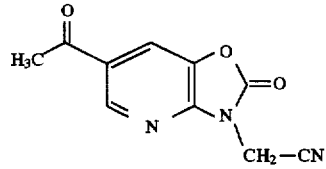

M.p.=170°–172° C.

IR (KBr): 1790 cm⁻¹ (CO carbamate), 1670 cm⁻¹ (CO ketone)

$^1$H NMR (CDCl$_3$), δ(ppm): 2.64 (s, CH$_3$, 3H); 4.85 (s, NCH$_2$, 2H); 8.03 (d, H$_7$, 1H, J$_{5,7}$=1.5 Hz); 8.79 (d, H$_5$, 1H, J$_{5,7}$=1.5 Hz).

EXAMPLE 4

6-ACETYLOXAZOLO[4,5-b]PYRIDIN-2(3H)-ONE

Method A: Decyanomethylation 3-cyanomethyl-6-acetyloxazolo[4,5-b]pyridin-2(3H)-one from Example 3 (1 g) is dissolved in ethanol (25 ml) and then platinum oxide (250 mg) is added. The solution is stirred at room temperature under a hydrogen atmosphere. After the catalyst has been filtered off, the solvent is evaporated off under reduced pressure. The title product is purified by flash chromatography on silica gel (eluant: dichloromethane/methanol: 95/5). The yield obtained is 98%.

Method B : Acetylation then debenzylation
Step 1: 6-acetyl-2-benzyloxyoxazolo[4,5-b]pyridine The method of operation is the same as that used for the synthesis of the compound of Example 1 (coupling with 1-ethoxy-1-(trimethylstannyl)ethylene), 2-benzyloxy-6-bromooxazolo[4,5-b]pyridine from Preparation 4 being used instead of the 6-bromo-3-methyloxazolo[4,5-b]pyridin-2(3H)-one from Preparation 2. The yield obtained is 78%.

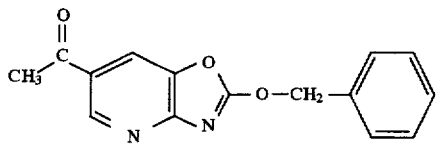

M.p.=180°–182° C.
IR (KBr): 1740 cm$^{-1}$ —C=N—, 1670 cm$^{-1}$ (CO ketone)
$^1$H NMR (CDCl$_3$), δ(ppm): 2.50 (s, CH$_3$, 3H); 5.48 (s, NCH$_2$, 2H); 7.53 (d, H$_7$, 1H, J$_{5,7}$=1.5 Hz); 7.35–7.48 (m, H$_{arom}$, 5H); 7.96 (d, H$_5$, 1H, J$_{5,7}$=1.5 Hz).

Step 2: 6-acetyloxazolo[4,5-b]pyridin-2(3H)-one 6-acetyl-2-benzyloxyoxazolo[4,5-b]pyridine from the preceding Step (1 g) is dissolved in methanol (25 ml) and then palladium-on-carbon (100 mg) is added. The solution is stirred at room temperature under a hydrogen atmosphere. After the catalyst has been filtered off, the solvent is evaporated off under reduced pressure. The title product is purified by flash chromatography on silica gel (eluant: dichloromethane/methanol:95/5). The yield obtained is 95%.

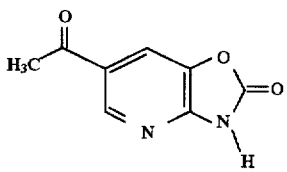

M.p.=222°–224° C. (H2O)
IR (KBr): 3500–3200 cm$^{-1}$ (NH), 1750 cm$^{-1}$ (CO carbamate), 1670 cm$^{-1}$ (CO ketone)
$^1$H NMR (CDCl$_3$+D$_2$O), δ: 2.22 (s, CH$_3$, 3H); 7.87 (s, H$_7$, 1H); 8.66 (d, H$_5$, 1H).

EXAMPLE 5

3-METHYL-6-BENZOYLOXAZOLO[4,5-b]PYRIDIN-2(3-ONE

Step 1: 3-methyl-6-benzyloxazolo[4,5-b]pyridin-2(3H)-one

Zinc (227 mg, 3.48 mmol) is suspended in tetrahydrofuran (10 ml) and 1,2-dibromoethane (0.22 ml, 0.2 mmol) is added. The mixture is heated at 60° C. for 3 minutes, the solution is allowed to cool until the temperature is 35° C., and trimethylsilyl chloride (0.06 ml, 0.5 mmol) is slowly added. Stirring is maintained for 30 minutes and then benzyl bromide (0.11 ml, 0.9 mmol) is added. Wait a further 30 minutes before introducing 6-bromo-3-methyloxazolo[4,5-b]pyridin-2(3H)-one (200 mg, 0.87 mmol) and tetrakis (triphenylphosphine)palladium (4 mg). Heat at 50° C. for 20 minutes. After the solution has been cooled, the zinc is removed by filtration, the filtrate is taken up in water, and then a 10% aqueous hydrochloric acid solution is added until the aqueous phase becomes clear. Extraction is carried out with dichloromethane. The organic phase is dried over magnesium sulfate and filtered, and then the solvent is evaporated off under reduced pressure. The title product is purified by chromatography on silica gel (eluant: dichloromethane). The yield obtained is 91%.

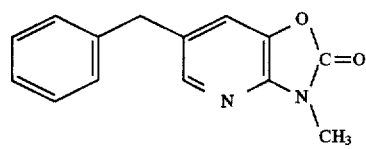

M.p.=127°–129° C.
IR (KBr): 1780 cm$^{-1}$ (CO carbamate)
$^1$H NMR (CDCl$_3$), δ(ppm): 3.46 (s, 3H, NCH$_3$); 4.00 (s, 2H, CH$_2$); 7.14–7.35 (m, 6H, H$_7$+5H$_{arom}$); 8.02 (d, 1H, H$_5$, J$_{5,7}$=1.5 Hz).

Step 2: 3-methyl-6-benzoyloxazolo[4,5-b]pyridin-2(3H)-one

Chromium(VI) oxide (5 mg, 0.05 mmol) is suspended in dichloromethane (25 ml) and then tert-butyl hydroperoxide (1.08 ml, 8 mmol) is added dropwise. 6-benzyl-3-methyloxazolo[4,5-b]pyridin-2-one from Step 1 (236 mg, 1 mmol) is slowly added to the solution. When the colour of the reaction mixture is yellow, the same quantity of chromium(VI) oxide and of tert-butyl hydroperoxide is added. Stirring is maintained for a further 24 hours. After the mixture has been filtered over Celite and the solvent has been evaporated off under reduced pressure, the title product is purified by chromatography on silica gel (eluant: dichloromethane). The yield obtained is 82%.

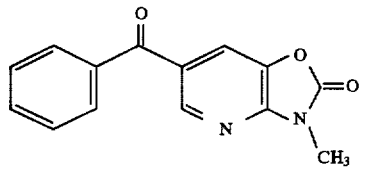

M.p.=131°–133° C. (i-PrOH)
IR (KBr): 1790 cm$^{-1}$ (CO carbamate), 1635 cm$^{-1}$ (CO ketone)
$^1$H NMR (CDCl$_3$), δ(ppm): 3.55 (s, NCH$_3$, 3H); 7.48–7.56 (m, H$_{arom}$, 2H); 7.60–7.67 (m, H$_{arom}$, 1H); 7.78 (d, H$_{arom}$, 2H, J=7.4 Hz); 7.89 (d, H$_7$, 1H, J$_{5,7}$1.5 Hz); 8.58 (d, H5, 1H, J$_{5,7}$=1.5 Hz).

EXAMPLE 6

6-BENZOYLOXAZOLO[4,5-b]PYRIDIN-2(3H)-ONE

The method of operation is the same as that used for the synthesis of the compound of Example 5. 6-benzyloxazolo

[4,5-b]pyridin-2(3H)-one is used instead of 6-benzyl-3-methyloxazolo[4,5-b]pyridin-2(3H)-one. The yield obtained is 50%.

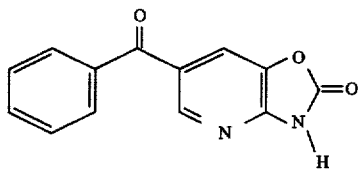

M.p.=196°–198° C.

IR (KBr): 1750 cm$^{-1}$ (CO carbamate), 1650 cm–1 (CO ketone)

$^1$H NMR (DMSO+D$_2$O); δ(ppm) 7.54–7.62 (m, H$_{arom}$, 2H); 7.67–7.79 (m, H$_{arom}$, 3H); 7.94 (d, H$_7$, 1H, J$_{5,7}$=1.5 Hz); 8.38 (d, H$_5$, 1H, J$_{5,7}$1.5 Hz).

EXAMPLE 7

6-ACETYL-3-(2-PHENYLETHYL)OXAZOLO[4,5-b]PYRIDIN-2(3H)-ONE

By proceeding in the same manner as for the synthesis of the compound of Example 1 (coupling with butyl vinyl ether), but replacing 6-bromo-3-methyl-oxazolo[4,5-b]pyridin-2(3H)-one with 6-bromo-3-(2-phenylethyl)oxazolo[4,5-b]pyridin-2(3H)-one (Preparation 5), the title compound is obtained in a yield of 75%.

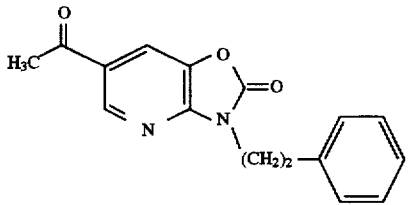

M.p.: 210°–212° C.

IR (KBr): 1765 cm$^{-1}$ (CO carbamate), 1675 cm$^{-1}$ (CO ketone)

$^1$H NMR (CDCl$_3$); δ(ppm): 2.59 (s, CH$_3$, 3H); 3.13 (dd, CH$_2$, 2H, J$_1$=8.1 Hz, J$_2$7.4 Hz); 4.18 (dd, NCH$_2$, 2H, J$_1$=8.1 Hz, J$_2$=7.4 Hz); 7.15–7.28 (m, H$_{arom}$, 5H); 7.88 (d, H$_7$, 1H, J$_{5,7}$=1.5 Hz); 8.69 (d, H$_5$, 1H, J$_{5,7}$=1.5 Hz).

EXAMPLE 8

6-ACETYL-3-(2-CYANOETHYL)OXAZOLO[4,5-b]PYRIDIN-2(3H)-ONE

By proceeding in the same manner as for the synthesis of the compound of Example 1 (coupling with butyl vinyl ether), but replacing 3-methyl-6-bromo-oxazolo[4,5-b]pyridin-2(3H)-one with 3-(2-cyanoethyl)-6-bromooxazolo[4,5-b]pyridin-2(3H-one (Preparation 7), the title compound is obtained in a yield of 74%.

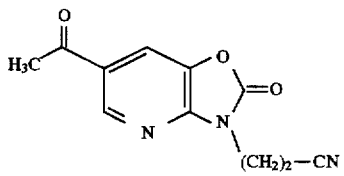

M.p.: 152°–154° C.

IR (KBr): 2240 cm$^{-1}$ (CN), 1780 cm$^{-1}$ (CO carbamate), 1670 cm$^{-1}$ (CO ketone)

$^1$H NMR (CDCl$_3$); δ(ppm): 2.65 (s, CH$_3$, 3H); 3.01 (t, CH$_2$, 2H, J=6.6 Hz); 4.81 (t, NCH$_2$, 2H, J=6.6 Hz); 8.01 (d, H$_7$, 1H, J$_{5,7}$=1.5 Hz); 8.77 (d, H$_5$, 1H, J$_{5,7}$=1.5 Hz).

EXAMPLE 9

6-ACETYL-3-[2-(PYRIDIN-2-YL)ETHYL]OXAZOLO[4,5-b]PYRIDIN-2(3H)-ONE

By proceeding in the same manner as for the synthesis of the compound of Example 1 (coupling with butyl vinyl ether), but replacing 6-bromo-3-methyl-oxazolo[4,5-b]pyridin-2(3H)-one with 6-bromo-3-[2-(pyridin-2-yl)ethyl]oxazolo[b]pyridin-2(3H)-one (Preparation 8), the title compound is obtained in a yield of 25%.

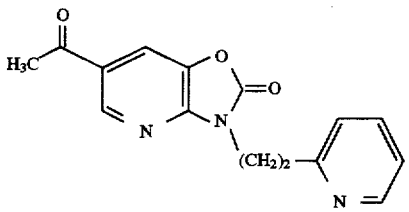

M.p.: 138°–140° C.

IR (KBr): 1790 cm$^{-1}$ (CO carbamate), 1675 cm$^{-1}$ (CO ketone)

$^1$H NMR (CDCl$_3$); δ(ppm): 2.62 (s, CH$_3$, 3H); 3.34 (t, CH$_2$, 2H, J=7.4 Hz); 4.40 (t, NCH$_2$, 2H, J=7.4 Hz); 7.10–7.18 (m, H$_{arom}$, 2H); 7.58 (t, H$_{arom}$, 1H, J=7.4 Hz); (d, H$_7$, 1H, J$_{5,7}$=1.5 Hz); 8.49 (d, H$_{arom}$, 1H, J=5.2 Hz); 8.71 (d, H$_5$1H, J$_{5,7}$=1.5 Hz).

EXAMPLE 10

6-ACETYL-3-[2-(PYRIDIN-4-YL)ETHYL]OXAZOLO[4,5-b]PYRIDIN-2(3H)-ONE

By proceeding in the same manner as for Example 1, but using 6-bromo-3-[2-(pyridin-4-yl)ethyl]oxazolo[4,5-b]pyridin-2(3H)-one (Preparation 9), the title compound is obtained in a yield of 50%.

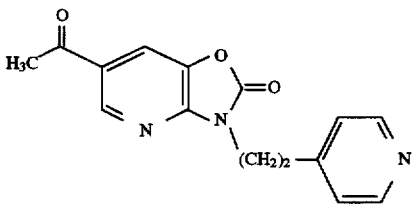

M.p.: 148°–150° C.

IR (KBr): 1790 cm$^{-1}$ (CO carbamate), 1675 cm$^{-1}$ (CO ketone)

$^1$H NMR (CDCl$_3$); δ(ppm): 2.63 (s, CH$_3$, 3H); 3.20 (t, CH$_2$, 2H, J=7.4 Hz); 4.26 (t, NCH$_2$, 2H, J=7.4 Hz); 7.19 (d, H$_{arom}$, 2H, J=5.9 Hz); 7.94 (d, H$_7$, 1H, J$_{5,7}$=1.5 Hz), 8.52 (d, H$_{arom}$, 2H, J=5.9 Hz); 8.72 (d, H$_5$, 1H, J$_{5,7}$=1.5 Hz).

EXAMPLE 11

3-METHYL-6-PROPIONYLOXAZOLO[4,5-b]PYRIDIN-2(3H)-ONE

By proceeding in the same manner as for Example 1 (coupling with butyl vinyl ether), but replacing butyl vinyl ether with ethyl-1-propenyl ether, the title compound is obtained in a yield of 40%.

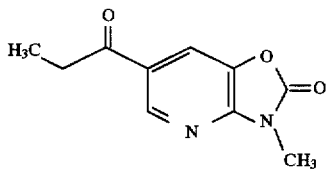

M.p.: 110°–112° C.

IR (KBr): 1800 cm$^{-1}$ (CO carbamate), 1670 cm$^{-1}$ (CO ketone)

$^1$H NMR (CDCl$_3$); δ(ppm): 1.26 (t, CH$_3$, 3H, J=7.4 Hz); 3.02 (m, CH$_2$, 2H); 3.55 (s, NCH$_3$, 3H); 7.98 (d, H$_7$, J$_{5,7}$=1.5 Hz); 8.79 (d, H$_5$, J$_{5,7}$=1.5 Hz).

EXAMPLE 12

1,3-DIHYDRO-1,3,3-TRIMETHYL-5-ACETYL-2H-PYRROLO[2,3-b]PYRIDIN-2-ONE

Under argon, suspend 482 mg (11.37 mmol) of lithium chloride and 90 mg (7.84×10−5 mol) of tetrakis (triphenylphosphine)palladium in 10 ml of anhydrous toluene. Add to that suspension a solution of 1 g (3.92 mmol) of 1,3-dihydro-1,3,3-trimethyl-5-bromo-2H-pyrrolo[2,3-b]pyridin-2-one and 1.46 mg (4.04 mmol) of (1-ethoxyvinyl) tributyltin in 20 ml of anhydrous toluene. After 5 hours at reflux, evaporate off the solvent and take up the residue in a 1:1 mixture (30 ml) of dioxane and 10% hydrochloric acid. After 30 minutes' stirring at room temperature, evaporate off the dioxane. Filter off the resulting tin salts over Celite. Extract the filtrate with dichloromethane and dry over magnesium sulfate. After purification on a silica column, 780 mg of the title product are obtained in a yield of 90%

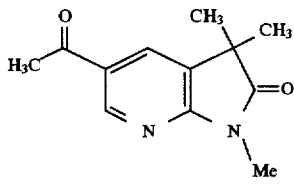

M.p.: 99°–100° C.

$^1$H NMR (CDCl$_3$); δ(ppm): 1.43 (s, 6H, 2×CH$_3$); 2.62 (s, 3H, CH$_3$—C=O); 3.35 (s, 3H, CH$_3$); 8.00 (d, 1H, H$_4$); 8.29 (d, 1H, H$_6$).

EXAMPLE 13

1,3-DIHYDRO-1-METHYL-5-ACETYL-2H-PYRROLO[2,3-b]PYRIDIN-2-ONE

By proceeding in the same manner as for the synthesis of the compound of Example 12, but replacing the 1,3-dihydro-1,3,3-trimethyl-5-bromo-2H-pyrrolo[2,3-b]pyridin-2-one with 1,3-dihydro-1-methyl-5-bromo-2H-pyrrolo[2,3-b]pyridin-2-one, the title compound is obtained in a yield of 84%.

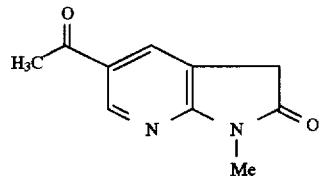

IR: 1705,1670 cm$^{-1}$ $^1$H NMR (CDCl$_3$); δ(ppm): 2.58 (s, 3H, CH$_3$—C=O); 3.32 (s, 3H, CH$_3$); 3.58 (s, 2H, CH$_2$); 8.04 (s, 1H, H$_4$); 8.78 (s, 1H, H$_6$).

EXAMPLE 14

6-(1-PHENYL-1-HYDROXYMETHYL)-3-METHYLOXAZOLO[4,5-b]PYRIDIN-2(3H)-ONE

Add 42 mg (1.1 mmol) of sodium borohydride to a previously prepared solution of 254 mg (1 mmol) of 6-benzoyl-3-methyloxazolo[4,5-b]pyridin-2(3H)-one in 20 ml of anhydrous methanol. Concentrate the reaction mixture to dryness under reduced pressure after stirring for 5 hours at room temperature, then take up the residue in water and isolate by filtration the resulting product; the title product is obtained in a yield of 84%.

EXAMPLE 15

5-BENZOYL-1-METHYL-1,3-DIHYDRO-2H-PYRROLO[2,3-b]PYRIDIN-2-ONE

Step 1: 5-benzyl-1-methyl-1,3-dihydro-2H-pyrrolo[2,3-b]pyridin-2-one

The title compound is obtained in a yield of 20% by proceeding as for Step 1 of Example 5, but replacing 6-bromo-3-methyloxazolo[4,5-b]pyridin-2(3H)-one with 1,3-dihydro-5-bromo-1-methyl-2H-pyrrolo[2,3-b]pyridin-2-one.

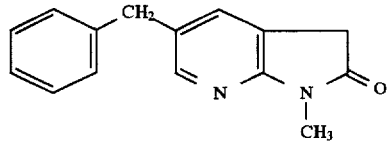

$^1$H NMR (CDCl$_3$); δ(ppm): 3.30 (s, 3H, N—CH$_3$); 3.48 (s, 2H, CH$_2$—C=O); 3.94 (s, 2H, CH$_2$—Ph); 7.15–7.33 (m, 6H, H$_{arom}$ +H$_4$); 8.08 (s, 1H, H$_6$).

Step 2: 5-benzyl-3,3-dibromo-1-methyl-1,3-dihydro-2H-pyrrolo[2,3-b]pyridin-2-one Add 60 mg of N-bromosuccinimide and a spatula tip of dibenzoyl peroxide to a previously prepared solution of 40 mg of the compound of Step 1 in carbon tetrachloride. Heat at reflux for 1 hour in order to concentrate to dryness, and purify the resulting crude product by chromatography on a silica column (eluant: petroleum ether/ethyl acetate: 7/3).

The title product is obtained in a yield of 72%.

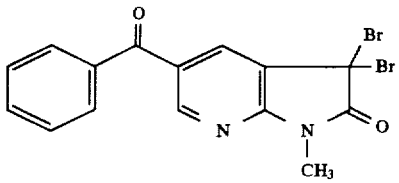

$^1$H NMR (CDCl$_3$); δ(ppm): 3.40 (s, 3H, CH$_3$); 7.54 (t, 2H, J=7.35 Hz, H$_{arom}$); 7.65 (d, 1H, J=7.35 Hz, H$_{arom}$); 7.80 (d, 2H, J=7.35 Hz, H$_{arom}$); 8.33 (d, 1H, J=2.2 Hz, H$_4$); 8.66 (d, 1H, J=2.2 Hz, H$_6$).

Step 3: 5-benzoyl-1-methyl-1,3-dihydro-2H-pyrrolo[2,3-b]pyridin-2-one

Add a spatula tip of zinc to a solution of 40 mg of the compound of Step 2 in acetic acid. After 30 minutes' stirring, concentrate to dryness under reduced pressure, take up in water and extract with dichloromethane. The crude product obtained by concentrating to dryness is purified by chromatography on a silica column (eluant: petroleum ether/ethyl acetate, 6/4).

The title product is obtained in the form of an oil in a yield of 60%.

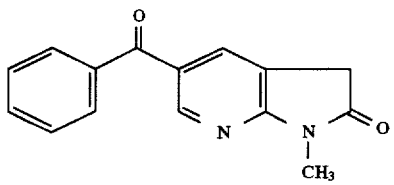

$^1$H NMR (CDCl$_3$); δ(ppm): 3.37 (s, 3H, N—CH$_3$); 3.64 (s, 2H, CH$_2$=O); 7.53 (t, 2H, J=7.35 Hz, H$_{arom}$); 7.64 (d, 1H, J=7.35 Hz, H$_{arom}$); 7.79 (d, 2H, J=7.35 Hz, H$_{arom}$); 8.02 (d, 1H, J=1.2 Hz, H$_4$); 8.63 (d,1H, J=1.2 Hz, H$_6$).

EXAMPLE 16

3-METHYL-6-[(4-PHENYLPIPERAZIN-1-YL)METHYL]OXAZOLO[4,5-b]PYRIDIN-2(3H)-ONE 6-bromomethyl-3-methyloxazolo[4,5-b]pyridin-2(3H)-one of Preparation 14 (1 g, 4.1 mmol) is dissolved in 1,4-dioxane (25 ml). N-phenylpiperazine (0.70 g, 4.3 mmol) and triethylamine (0.62 g, 6.2 mmol) are added in succession to the reaction mixture. The solution is stirred for 5 hours at room temperature and under an inert atmosphere. After the solvent has been evaporated off under reduced pressure, the residue is taken up in water and then extracted with dichloromethane; the organic phase is dried over magnesium sulfate and filtered, and then the solvent is evaporated off. The title product is purified by chromatography on silica gel (eluant: dichloromethane/methanol: 98/2). The yield obtained is 96%.

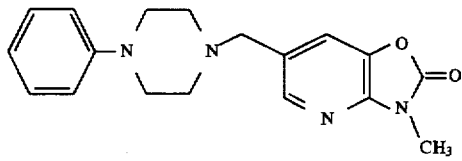

M.p.=130°–132° C. (i-PrOH)
IR (KBr): 1775 cm$^{-1}$ (CO carbamate)

$^1$H NMR (CDCl$_3$), δ(ppm): 2.61 (dd, 2×CH$_{2piper}$, 4H, J$_1$=5.2 Hz, J$_2$=4.4 Hz); 3.19 (dd, 2×CH$_{2piper}$, 4H, J$_1$=5.2 Hz, J$_2$=4.4 Hz); 3.48 (s, NCH$_3$, 3H); 3.58 (s, CH$_2$, 2H); 6.86 (t, H$_{arom}$, 1H, J=7.3 Hz); 6.92 (d, H$_{arom}$2H, J=8.8 Hz); 7.24 (d, H$_{arom}$ 2H, J=8.8 Hz); 7.51 (d, H$_7$, 1H, J$_{5,7}$=1.8 Hz); 8.05 (d, H$_5$, 1H, J$_{5,7}$=1.8 Hz). MS (IC/NH$_3$): m/z: 325 (M+1).

EXAMPLE 17

3-METHYL-6-(MORPHOLINOMETHYL)OXAZOLO[4,5-b]PYRIDIN-2(3H)-ONE

The method of operation is the same as that used for the synthesis of the compound of Example 16. Morpholine is used instead of N-phenylpiperazine. The yield obtained is 90%.

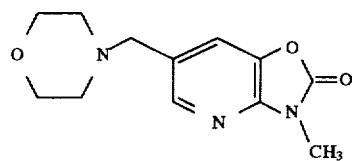

M.p.=143°–145° C. (i-PrOH)
IR (KBr): 1775 cm$^{-1}$ (CO carbamate)

$^1$H NMR (CDCl$_3$), δ(ppm): 2.46 (dd, 2×CH$_{2morph}$, 4H, J$_1$=5.2 Hz, J$_2$=4.3 Hz); 3.49 (s, NCH$_3$, 3H); 3.52 (s, CH$_2$, 2H); 3.71 (dd, 2×CH$_{2morph}$, 4H, J$_1$=5.2 Hz, J$_2$=4.3 Hz); 7.50 (d, H$_7$, 1H, J$_{5,7}$=1.8 Hz); 8.03 (d, H$_5$, 1H, J$_{5,7}$=1.8 Hz). MS (IC/NH$_3$): m/z: 250 (M+1).

EXAMPLE 18

3-METHYL-6-[2-(4-PHENYLPIPERAZIN-1-YL)ETH-1-YL]OXAZOLO[4,5-b]PYRIDIN-2(3H)-ONE 3-methyl-6-[2-(p-toluenesulfonyloxy)ethyl]oxazolo[4,5-b]pyridin-2(3-one of Preparation 15 (210 mg, 1.2 mmol) is dissolved in 1,4-dioxane (8 ml). N-phenyl-piperazine (0.10 ml, 1.38 mmol) and triethylamine (0.18 ml, 1.3 mmol) are added in succession to the reaction mixture. Stirring is maintained at room temperature for 24 hours. After the solvent has been evaporated off under reduced pressure, the residue is taken up in water. Extraction is carried out with dichloromethane and the organic phase is dried over magnesium sulfate and filtered, and then the solvent is evaporated off. The title product is purified by chromatography on silica gel (eluant: dichloromethane/methanol: 95/5). The yield obtained is 91%.

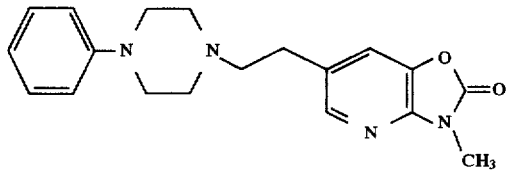

M.p.=80°–82° C. (washing with ether)
IR (KBr): 1790 cm$^{-1}$ (CO carbamate)

$^1$H NMR (CDCl$_3$), δ(ppm): 2.64–2.72 (m, CH$_2$+2×CH$_{2piper}$, 6H); 2.88 (dd, CH$_2$, 2H, J$_1$=8.0 Hz, J$_2$=7.1 Hz); 3.24 (dd, 2×CH$_{2piper}$, 4H, J$_1$=5.6 Hz, J$_2$4.8 Hz, J$_3$2 4.8 Hz); 3.49 (s, NCH$_3$, 3H); 6.88 (t, H$_{arom}$, 1H, J=7.1 Hz); 6.95 (d, H$_{arom}$, 2H, J=7.9 Hz); 7.24–7.32 (m, H$_{arom}$, 2H); 7.35 (d, H$_7$, 1H, J$_{5,7}$=1.6 Hz); 8.01 (d, H$_5$, 1H, J$_{5,7}$=1.6 Hz).

EXAMPLE 19

3-METHYL-6-(2-MORPHOLINOETHYL) OXAZOLO[4,5-b]PYRIDIN-2(3H)-ONE

By proceeding as for Example 18, but replacing phenylpiperazine with morpholine, 3-methyl-6-(2-morpholinoethyl)oxazolo[4,5-b]pyridin-2(3H-one is obtained.

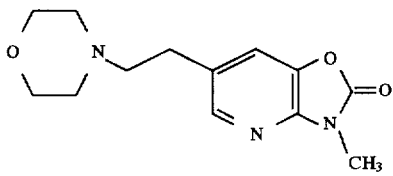

Oil

IR (KBr): 1790 cm$^{-1}$ (CO carbamate)

$^1$H NMR (CDCl$_3$), δ(ppm): 2.50 (dd, 2×CH$_{2morph}$, 4H, J$_1$=5.2 Hz, J$_2$=4.4 Hz); 2.59 (t, CH$_2$, 2H, J=7.3 Hz); 2.83 (t, CH$_2$, 2H, J=7.3 Hz); 3.46 (s, NCH$_3$, 3H); 3.73 (dd, 2×CH$_{2morph}$, 4H, J$_1$=5.2 Hz, J$_2$=4.4 Hz); 7.33 (d, H$_7$, 1H, J$_{5,7}$=1.5 Hz); 7.97 (d, H$_5$, J$_{5,7}$=1.5 Hz).

EXAMPLE 20

3-METHYL-6-[3-(4-PHENYLPIPERAZIN-1-YL) PROP-1-YL]OXAZOLO[4,5-b]PYRIDIN-2(3H)-ONE

The method of operation is the same as that used for the synthesis of the compound of Example 18, 3-methyl-6-[3-(p-toluenesulfonyloxy)-n-prop-1-yl]oxazolo-[4,5-b]pyridin-2(3H)-one from Preparation 16 being used instead of 3-methyl-6-[2-(p-toluenesulfonyloxy)ethyl]oxazolo[4,5-b]pyridin-2(3H)-one.

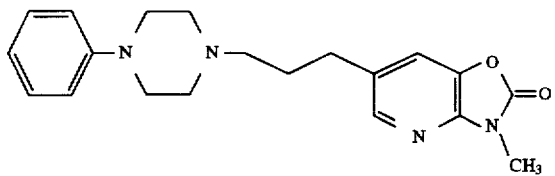

M.p. <60° C. (washing with ether)

IR (KBr): 1785 cm$^{-1}$ (CO carbamate)

$^1$H NMR (CDCl$_3$), δ(ppm): 1.79–1.90 (m, CH$_2$, 2H); 2.41 (t, CH$_2$, 2H, J=7.4 Hz); 2.59 (dd, 2×CH$_{2piper}$, 4H, J$_1$=5.1 Hz, J$_2$=4.4 Hz); 2.71 (t, CH$_2$, 2H, J=7.4 Hz); 3.21 (dd, 2×CH$_{2piper}$, 4H, J$_1$=5.1 Hz, J$_2$=4.4 Hz); 3.49 (s, NCH$_3$, 3H); 6.85 (t, H$_{arom}$, 1H, J=7.4 Hz); 6.92 (d, H$_{arom}$, 2H, J=8.1 Hz); 7.22–7.29 (m, H$_7$+H$_{arom}$, 3H); 7.96 (d, H$_5$, 1H, J$_{5,7}$=1.5 Hz).

EXAMPLE 21

3-METHYL-6-(3-MORPHOLINO-N-PROP-1-YL) OXAZOLO[4,5-b]PYRIDIN-2(3H)-ONE

By proceeding as for Example 20, but replacing phenylpiperazine with morpholine, 3-methyl-6-(3-morpholino-n-prop-1-yl)oxazolo[4,5-b]pyridin-2(3H-one is obtained in a yield of 83%.

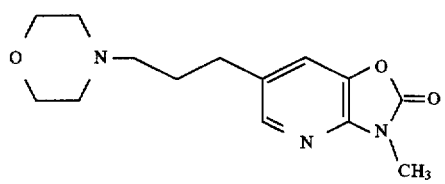

M.p. <80° C. (washing with ether)

IR (KBr): 1790 cm$^{-1}$ (CO carbamate)

$^1$H NMR (CDCl$_3$), δ(ppm): 1.75–1.90 (quint., CH$_2$, 2H, J=7.4 Hz); 2.37 (t, CH$_2$2H, J=7.4 Hz); 2.44 (t, 2×CH$_{2morph}$, 4H, J=4.4 Hz); 2.71 (t, CH$_2$, 2H, J=7.4 Hz); 3.49 (s, NCH$_3$, 3H); 3.74 (dd, 2×CH$_{2morph}$, 4H, J=4.4 Hz); 7.28 (d, H$_7$, 1H, J$_{5,7}$=1.5 Hz); 7.97 (d, H$_5$, J$_{5,7}$=1.5 Hz).

EXAMPLE 22

3-METHYL-6-[2-(4-PHENYLPIPERAZIN-1-YL) ACETYL]OXAZOLO[4,5-b]PYRIDIN-2(3H)-ONE

The method of operation is the same as that used for the synthesis of the compound of Example 16, 3-methyl-6-(bromoacetyl)oxazolo[4,5-b]pyridin-2(3H)-one from Preparation 17 being used instead of 3-methyl-6-(bromomethyl) oxazolo[4,5-b]pyridin-2(3H)-one.

The yield obtained is 84%.

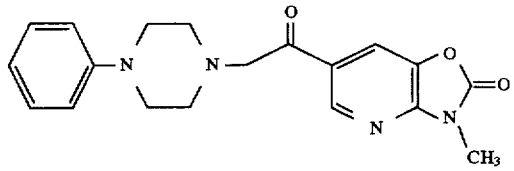

M.p.: 201°–203° C. (washing with ether)

IR (KBr): 1775 cm$^{-1}$ (CO carbamate)

$^1$H NMR (CDCl$_3$), δ(ppm): 2.75, (dd, 2×CH$_{2piper}$, 4H, J$_1$=5.1 Hz, J$_2$=4.4 Hz); 3.24, (dd, 2×CH$_{2piper}$, 4H, J$_1$=5.1 Hz, J$_2$=4.4 Hz); 3.52 (s, NCH$_3$, 3H); 3.78 (s, CH$_2$2H); 6.85 (t, H$_{arom}$, 1H, J=7.4 Hz); 6.92 (d, H$_{arom}$, 2H, J=8.1 Hz); 7.21–7.30 (m, H$_{arom}$, 2H); 8.05 (d, H$_7$, 1H, J$_{5,7}$=1.5 Hz); 8.99 (d, H$_5$, J$_{5,7}$=1.5 Hz).

EXAMPLE 23

3-METHYL-6-(2-MORPHOLINOACETYL) OXAZOLO[4,5-b]PYRIDIN-2(3H)-ONE

By proceeding as for Example 22, but replacing phenylpiperazine with morpholine, 3-methyl-6-(2-morpholinoacetyl)oxazolo[4,5-b]pyridin-2(3H)-one is obtained in a yield of 86%.

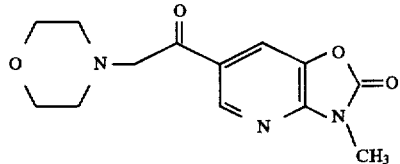

M.p.: 185°–187° C. (washing with ether)

IR (KBr): 1775 cm$^{-1}$ (CO carbamate)

$^1$H NMR (CDCl$_3$), δ(ppm): 2.57, (dd, 2×CH$_{2morph}$, 4H, J$_1$=5.2 Hz, J$_2$=4.4 Hz); 3.51 (s, NCH$_3$, 3H); 3.71 (s, CH$_2$, 2H); 3.73 (dd, 2×CH$_{2morph.}$, 4H, J$_1$=5.2 Hz, J$_2$=4.4 Hz); 8.01 (d, H$_7$, 1H, J$_{5,7}$=1.5 Hz); 8.93 (d, H$_5$, J$_{5,7}$=1.5 Hz).

EXAMPLE 24

3-METHYL-6-[2-(4-PHENYLPIPERAZIN-1-YL)-1-HYDROXYETHYL]OXAZOLO[4,5-b]PYRIDIN-2(3H)-ONE

Method A: From 3-methyl-6-[2-(4-phenylpiperazin-1-yl)acetyl]oxazolo[4,5-b]pyridin-2(3H)-one 3-methyl-6-[2-(4-phenylpiperazin-1-yl)acetyl]oxazolo[4,5-b]pyridin-2(3H)-one of Example 22 (352 mg, 1 mmol) is dissolved in anhydrous methanol (15 ml), then sodium borohydride (42 mg, 1.1 mmol) is added to the solution. Stirring is maintained at room temperature for 5 hours. After the addition of water to the reaction mixture, the title product formed is filtered and then dried in vacuo. The yield obtained is 95%.

Method B: From 3-methyl-6-(2-bromo-1-hydroxyethyl)-oxazolo[4,5-b]pyridin-2(3H)-one The procedure is as for Example 22, but 3-methyl-6-(bromoacetyl)oxazolo[4,5-b]pyridin-2(3H)-one is replaced with 3-methyl-6-(2-bromo-1-hydroxyethyl)oxazolo[4,5-b]pyridin-2(3H)-one from Preparation 20. The yield obtained is 90%.

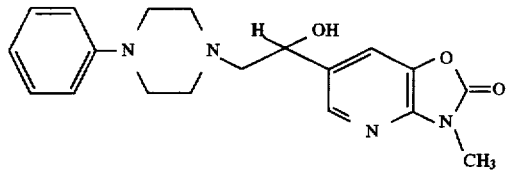

M.p.: 182°–184° C. (washing with ether)

IR (KBr): 3400–3100 (OH), 1775 (CO carbamate) cm$^{-1}$ $^1$H NMR (CDCl$_3$+D$_2$O), δ(ppm): 2.47–2.60 (m, NCH$_2$, 2H); 2.60–2.70 (m, CH$_{2piper.}$, 2H); 2.88–2.98 (m, CH$_{2piper.}$, 2H); 3.18–3.33 (m, 2×CH$_{2piper.}$, 4H); 3.48 (s, NCH$_3$, 3H); 4.83 (dd, CH, 1H, J$_1$=10.3 Hz, J$_2$=4.4 Hz); 6.88 (t, H$_{arom}$, 1H, J=7.4 Hz); 6.94 (d, H$_{arom}$, 2H, J=8.1 Hz); 7.29 (m, H$_{arom}$2H, J=8.1 Hz); 7.53 (d, H7, 1H, J$_{5,7}$=1.5 Hz); 8.10 (d, H$_5$, J$_{5,7}$=1.5 Hz).

EXAMPLE 25

3-METHYL-6-[2-MORPHOLINO-1-HYDROXYETHYL]OXAZOLO[4,5-b]PYRIDIN-2(3H)-ONE

Method A: From the aminoketone of Example 23

The method of operation is the same as that used for the synthesis of the compound of Example 24, Method A. The yield obtained is 98%.

Method B : From the bromoalcohol

The method of operation is the same as that used for the synthesis of the compound of Example 24, Method B. The yield obtained is 93%.

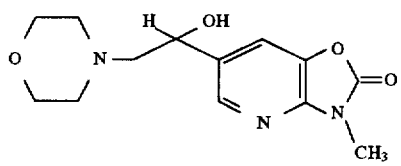

M.p.: 145°–147° C. (washing with ether)

IR (KBr): 3400–3100 cm$^{-1}$ (OH), 1775 cm$^{-1}$ (CO carbamate)

$^1$H NMR (CDCl$_3$+D$_2$O), δ(ppm): 2.36–2.56 (m, NCH$_2$+CH$_{2morph.}$, 4H); 2.68–2.78 (m, CH$_{2morph.}$, 2H); 3.48 (s, NCH$_3$, 3H); 3.66–3.80 (m, 2×CH$_{2morph.}$, 4H); 4.76 (dd, CH, 1H, J$_1$=10.4 Hz, J$_2$=3.9 Hz); 7.47 (d, H$_7$, 1H, J$_{5,7}$=1.5 Hz); 8.04 (d, H$_5$, J$_{5,7}$=1.5 Hz).

EXAMPLE 26

3-METHYL-6-[(4-(PYRIMID-2-YL)PIPERAZIN-1-YL)METHYL]OXAZOLO[4,5-b]PYRIDIN-2(3H)-ONE

The title compound is obtained by proceeding in the same manner as for Example 16, but replacing 4-phenylpiperazine with 4-(pyrimid-2-yl)piperazine.

EXAMPLE 27

3-METHYL-6-[(4-METHYLPIPERAZIN-1-YL)METHYL]OXAZOLO[4,5-b]PYRIDIN-2(3H)-ONE

The title compound is obtained by proceeding in the same manner as for Example 16, but replacing 4-phenylpiperazine with 4-methylpiperazine.

EXAMPLE 28

3-METHYL-6-[2-(4-BENZYLPIPERAZIN-1-YL)ACETYL]OXAZOLO[[4,5-b]PYRIDIN-2(3H)-ONE

The title compound is obtained by proceeding in the same manner as for Example 22, but replacing phenylpiperazine with 4-benzylpiperazine.

EXAMPLE 29

3-METHYL-6-{2-[4-(4-FLUOROPHENYL)PIPERAZIN-1-YL]ACETYL}OXAZOLO[4,5-b]PYRIDIN-2(3H)-ONE

The title compound is obtained by proceeding in the same manner as for Example 22, but replacing phenylpiperazine with 4-(4-fluorophenyl)piperazine.

EXAMPLE 30

3-METHYL-6-{2-[4-(3-TRIFLUOROMETHYLPHENYL)PIPERAZIN-1-YL]ACETYL}OXAZOLO[4,5-b]PYRIDIN-2(3H-ONE

The title compound is obtained by proceeding in the same manner as for Example 22, but replacing phenylpiperazine with 4-(3-trifluoromethylphenyl) piperazine.

EXAMPLE 31

3-METHYL-6-[2-(4-BENZHYDRYLPIPERAZIN-1-YL)1-HYDROXYETHYL]OXAZOLO[4,5-b]PYRIDIN-2(3H)-ONE

The title compound is obtained by proceeding in the same manner as for Example 24, but replacing phenylpiperazine with 4-benzhydrylpiperazine.

EXAMPLE 32

3-METHYL-6-{2-[4-(4,4'-DIFLUOROBENZHYDRYL)PIPERAZIN-1-YL]-1-HYDROXYETHYL}OXAZOLO[4,5-b]PYRIDIN-2(3H)-ONE

The title compound is obtained by proceeding in the same manner as for Example 24, but replacing phenylpiperazine with 4-(4,4'-difluorobenzhydryl) piperazine.

EXAMPLE 33

3-METHYL-6-[2-(3-AZASPIRO[5.5]UNDECAN-3-YL)ETH-1-YL]OXAZOLO[4,5-b]PYRIDIN-2(3H)-ONE

The title compound is obtained by proceeding in the same manner as for Example 16, but replacing phenylpiperazine with 3-azaspiro[5.5]undecane.

EXAMPLE 34

3-METHYL-6-[2-(3-AZABICYCLO[3.2.2]NONAN-3-YL)ETH-1-YL]OXAZOLO[4,5-b]PYRIDIN-2(3H)-ONE

The title compound is obtained by proceeding in the same manner as for Example 16, but replacing phenylpiperazine with 3-azabicyclo[3.2.2]nonane.

EXAMPLE 35

3-METHYL-6-{2-[4-(PYRID-2-YL)PIPERAZIN-1-YL]ACETYL}OXAZOLO[4,5-b]PYRIDIN-2(3H)-ONE

The title compound is obtained by proceeding in the same manner as for Example 22, but replacing phenylpiperazine with 4-(pyrid-2-yl)piperazine.

EXAMPLE 36

3-METHYL-6-(2-THIOMORPHOLINOACETYL)OXAZOLO[4,5-b]PYRIDIN-2(3H)-ONE

The title compound is obtained by proceeding in the same manner as for Example 22, but replacing phenylpiperazine with thiomorpholine.

EXAMPLE 37

3-METHYL-6-[2-(N,N-DIPROPYLAMINO)ACETYL]OXAZOLO[4,5-b]PYRIDIN-2(3H)-ONE

The title compound is obtained by proceeding in the same manner as for Example 22, but replacing phenylpiperazine with N,N-dipropylamine.

EXAMPLE 38

3-METHYL-6-(2-ANILINOACETYL)OXAZOLO[4,5-b]PYRIDIN-2(3H)-ONE

The title compound is obtained by proceeding in the same manner as for Example 22, but replacing phenylpiperazine with aniline.

EXAMPLE 39

3-METHYL-6-[2-(N-BENZYLAMINO)-1-HYDROXYETHYL]OXAZOLO[4,5-b]PYRIDIN-2(3H)-ONE

The title compound is obtained by proceeding in the same manner as for Example 24, but replacing phenylpiperazine with N-benzylamine.

EXAMPLE 40

3-METHYL-6-[2-(4-NAPHTH-1-YL)PIPERAZIN-1-YL1-HYDROXYETHYL]OXAZOLO[4,5-b]PYRIDIN-2(3H)-ONE

The title compound is obtained by proceeding in the same manner as for Example 24, but replacing phenylpiperazine with 4-(naphth-1-yl)piperazine.

EXAMPLE 41

3-METHYL-6-(2-PYRROLIDINOETHYL)OXAZOLO[4,5-b]PYRIDIN-2(3H)-ONE

The title compound is obtained by proceeding in the same manner as for Example 18, but replacing phenylpiperazine with pyrrolidine.

EXAMPLE 42

3-METHYL-6-(3-PIPERIDINO-n-PROP-1-YL)OXAZOLO[4,5-b]PYRIDIN-2(3H)-ONE

The title compound is obtained by proceeding in the same manner as for Example 20, but replacing phenylpiperazine with piperidine.

EXAMPLE 43

3-METHYL-6-[3-(3-AZABICYCLO[3.3.0]OCT-3-YL)-n-PROP-1-YL]OXAZOLO[4,5-b]PYRIDIN-2(3H)-ONE

The title compound is obtained by proceeding in the same manner as for Example 20, but replacing phenylpiperazine with 3-azabicyclo[3.3.0]octane.

EXAMPLE 44

3-BENZYL-6-[2-(4-PHENYLPIPERAZIN-1-YL)ACETYL]OXAZOLO [4,5-b]PYRIDIN-2(3H)-ONE

The title compound is obtained by proceeding in the same manner as for Example 22, but replacing 3-methyl-6-bromoacetyloxazolo[4,5-b]pyridin-2(3H)-one with 3-benzyl-6-bromoacetyloxazolo[4,5-b]pyridin-2(3H)-one from Preparation 21.

EXAMPLE 45

3-ETHYL-6-[(4-PHENYLPIPERAZIN-1-YL)METHYL]OXAZOLO[4,5-b]PYRIDIN-2(3H)-ONE

The title compound is obtained by proceeding in the same manner as for Example 16, but replacing 3-methyl-6-bromomethyloxazolo[4,5-b]pyridin-2(3H)-one with 3-ethyl-6-bromoethyloxazolo[4,5-b]pyridin-2(3H)-one from Preparation 22.

EXAMPLE 46

1,3-DIHYDRO-5-(4-PHENYLPIPERAZIN-1-YLMETHYL)-1-METHYL-2H-PYRROLO[2,3-b]PYRIDIN-2-ONE 1,3-dihydro-5-bromomethyl-1-methyl-2H-pyrrolo[2,3-b]pyridin-2-one from Preparation 18 (0.14 g, 0.6 mmol) is dissolved in dioxane (20 ml) at room temperature and under argon. Phenylpiperazine (0.1 ml, 0.66 mmol, 1.1 equiv.) and triethylamine (0.1 ml, 0.72 mmol, 1.2 equiv.) are added in succession at the same temperature. After 1 hour 30 minutes' reaction, the reaction mixture is concentrated under reduced pressure and the product is purified on a silica column (dichloromethane/methanol: 97:3). The title compound is obtained in the form of a yellow oil in a yield of 65%.

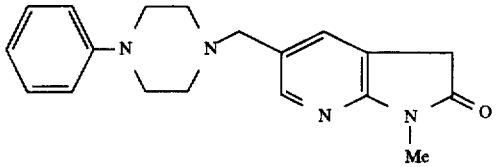

IR (film): =1719 cm$^{-1}$ (C=O)

$^1$H NMR (CDCl$_3$), δ(ppm): 2.57 (t, 4H, 2—CH$_{2piper.}$, J=5.2 Hz); 3.16 (t, 4H, 2×CH$_{2piper.}$, J=5.2 Hz); 3.27 (s, 3H, CH$_3$); 3.48 (s, 2H, CH$_2$); 3.50 (s, 2H, CH$_2$); 6.85–6.94 (m, 3H, H$_{Ar}$); 7.22–7.30 (m, 2H, H$_{Ar}$); 7.52 (s, 1H, H$_4$); 8.06 (s, 1H, H$_6$).

EXAMPLE 47

1,3-DIHYDRO-5-[2-(4-PHENYLPIPERAZIN-1-YL)ACETYL]-1-METHYL-2H-PYRROLO[2,3-b]PYRIDIN-2-ONE

Add 63 mg (3.9×10–4mol) of N-phenylpiperazine and then, very slowly, 0.08 ml (5.57'10–4 mol) of triethylamine to a previously prepared solution of 100 mg (3.72×10–4 mol) of 1,3-dihydro-5-bromoacetyl-1-methyl-2H-pyrrolo[2,3-b]pyridin-2-one (Preparation 19) in 3 ml of dioxane. After 30 minutes' stirring at room temperature, the resulting precipitate is removed by filtration and the filtrate is concentrated under reduced pressure to obtain the title product in a yield of 78%.

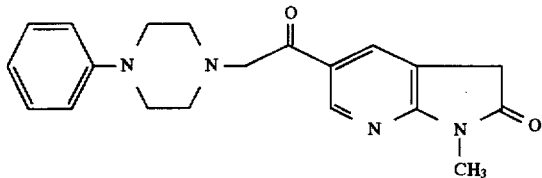

M.p.: 136°–137° C.

$^1$H NMR (CDCl$_3$), δ(ppm): 2.77–2.81 (m, H, CH$_{2piper.}$); 3.24–3.28 (m, 4H, CH$_{2piper.}$); 3.36 (s, 3H, N—CH$_3$); 3.59 (s, 2H, CH$_2$—C=O); 3.79 (s, 2H, CH$_{CH2}$—N); 6.86–6.99 (m, 3H, H$_{arom}$); 7.25–7.34 (m, 2H, H$_{arom}$); 8.12 (s, 1H, H$_4$); 9.05 (s, 1

EXAMPLE 48

1,3-DIHYDRO-5-[2-(4-PHENYLPIPERAZIN-1-YL)ACETYL]-1,3,3-TRIMETHYL-2H-PYRROLO[2,3-b]PYRIDIN-2-ONE

The title compound is obtained by proceeding as for Example 47, but replacing 1,3-dihydro-5-bromoacetyl-1-methyl-2H-pyrrolo[2,3-b]pyridin-2-one with 1,3-dihydro-5-bromoacetyl-1,3,3-trimethyl-2H-pyrrolo[2,3-b]pyridin-2-one (Preparation 23).

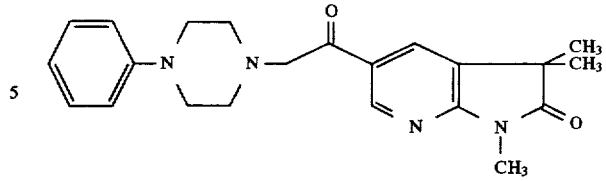

$^1$H NMR (CDCl$_3$), δ(ppm): 1.45 (s, 6H, 2—CH$_3$); 2.75–2.80 (m, 4H, 2—CH$_{2piper.}$); 3.25–3.30 (m, 4H, 2—CH$_{2piper.}$); 3.35 (s, 3H, N—CH$_3$); 3.80 (s, 2H, CH$_2$—C=O); 6.85–6.95 (m, 3H, H$_{arom}$); 7.25–7.30 (m, 2H, H$_{arom}$); 8.06 (s, 1H, H$_4$); 9.05 (s, 1H, H$_6$).

EXAMPLE 49

1,3-DIHYDRO-5-[2-(4-PHENYLPIPERAZIN-1-YL)-1-HYDROXYETHYL]-1-METHYL-2H-PYRROLO[2,3b]PYRIDIN-2-ONE

Add 8 mg (2×10–4 mol) of sodium borohydride to a previously prepared solution of 50 mg (1.43×10–4 mol) of 1,3-dihydro-5-[2-(4-phenylpiperazin-1-yl)acetyl]1-methyl-2H-pyrrolo[2,3-b]pyridin-2-one at 0° C. After 2 hours' stirring at room temperature, add 1 ml of acetic acid and concentrate the reaction mixture to dryness under reduced pressure. The crude product obtained is purified by chromatography on silica gel (eluant: methanol/dichloromethane, 5/95). The title product is obtained in the form of an oil in a yield of 40%.

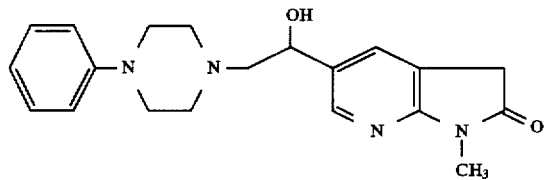

$^1$H NMR (CDCl$_3$), δ(ppm): 2.57–2.62 (m, 4H, CH$_{2piper.}$, CH$_2$N); 2.63–2.72 (m, 2H, CH$_{2piper.}$); 2.91–3.02 (m, 2H, CH$_{2piper.}$); 3.24–3.29 (m, 5H, N—CH$_3$, CH$_{2piper.}$); 3.53 (s, 2H, CH$_2$—C=O); 4.79–4.84 (m, 1H, CH—OH); 6.86–6.94 (m, 3H, H$_{arom}$); 7.25–7.30 (m, 2H, H$_{arom}$); 7.59 (s, 1H, H$_4$); 8.14 (s, 1H, H$_6$).

PHARMACOLOGICAL STUDY
A) INVESTIGATION OF THE ANALGESIC ACTIVITY
1) Cramps induced with acetic acid The analgesic potential of the products was investigated according to the KOSTER test, which is based on counting abdominal cramps induced in the rat by the intraperitoneal injection of acetic acid (Koster R., Anderson M., and De Beer E., J. Fed. Proc., (1959), 18, 412).

Male Wistar rats randomly divided into groups of 5 (weight 150±10 g) receive the test products per os 30 minutes before the intraperitoneal injection of 1 cm$^3$ of 1% acetic acid.

The number of cramps is counted during the 25 minutes which follow the injection.

The percentage activity was evaluated for each compound (% decrease in the number of cramps in the treated animals compared with the control animals).

2) Cramps induced with phenylbenzoquinone

The analgesic potential of the products was also investigated in accordance with the SIEGMUND test, which is based on counting the number of cramps induced in the mouse by the intraperitoneal injection of phenylbenzoquinone (Siegmund E., Cadmus R., *Proc. Sol. Exp. Biol. Med.*, (1957), 95, 729).

Male CD-1 mice randomly divided into groups of 5 receive the test products per os 30 minutes before the intraperitoneal injection of 0.25 cm3 of a 0.01% solution of phenylbenzoquinone in a 95:5 mixture of water and ethanol.

The number of cramps is counted between the 5th and the 15th minute after the injection of phenylbenzoquinone.

The percentage activity was evaluated for each compound (% decrease in the number of cramps in the treated animals compared with the control animals).

| PRODUCT | DOSE (mg/kg) | Acetic Acid Writhing, % inhibition | PBO Whrithing, % inhibition |
|---|---|---|---|
| Aspirin | 50 | 56% | 62% |
| Example 5 | 50 | 85% | 85% |
| Example 6 | 50 | 88% | |
| Example 13 | 50 | 96% | |
| Example 16 | 50 | 98% | 57% |
| Example 20 | 50 | | 100% |
| Example 22 | 50 | 97% | 53% |
| Example 24 | 50 | 86% | 97% |
| Example 46 | 50 | | 67% |
| Example 47 | 50 | | 90% |

It appears that the compounds of the invention have a very valuable antalgic activity which is very significantly higher than that of aspirin.

B) ACUTE TOXICITY STUDY

Acute toxicity was evaluated by the oral administration of increasing doses of the test compounds to groups comprising 3 male NMRI mice.

The animals were observed at regular intervals over a period of 24 hours following administration of the product.

It appears that the compounds of the invention seem particularly non-toxic, no death being observed using the test compounds up to a dose of 1024 mg/kg.

C) TABLETS EACH COMPRISING 15 mg OF 6-BENZOYL-3-METHYLOXAZOLO[4,5-b]PYRIDIN-2 (3H)-ONE formulation for the preparation of 1000 tablets:

| | |
|---|---|
| 6-benzoyl-3-methyloxazolo[4,5-b]pyridin-2(3H)-one | 15 g |
| wheat starch | 15 g |
| corn starch | 15 g |
| lactose | 65 g |
| magnesium stearate | 1 g |
| silica | 1 g |
| hydroxypropyl cellulose | 2 g |

D) TABLETS EACH COMPRISING 5 mg of 6-BENZOYL-3-METHYLOXAZOLO [4,5-b]PYRIDIN-2 (3H)-ONE

Formulation for the preparation of 1000 tablets:

| | |
|---|---|
| 6-benzoyl-3-methyloxazolo[4,5-b]pyridin-2(3H)-one | 5 g |
| caffeine | 120 g |
| corn starch | 66 g |
| lactose | 305 g |
| magnesium stearate | 1 g |
| silica | 1 g |
| hydroxypropyl cellulose | 2 g |

We claim:

1. A compound selected from those of formula (I):

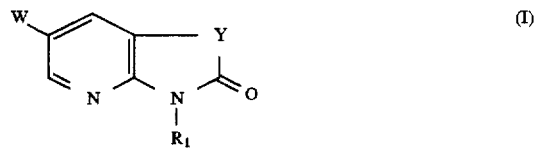

wherein:

$R_1$ is selected from hydrogen, alkyl, alkenyl, cyanoalkyl, and arylalkyl.

W is selected from —A—$R_2$ and

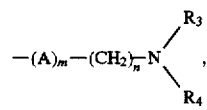

$R_2$ is selected from alkyl, cycloalkyl, cycloalkylalkyl, phenyl, phenylalkyl, naphthyl, and naphthylalkyl.

$R_3$ and $R_4$ are selected, each independently of the other, from hydrogen, alkyl, phenyl, phenylalkyl, cycloalkyl, and cycloalkylalkyl.

n is 1 to 4 inclusive, m is 0 or 1,

A is selected from

and

Y represents

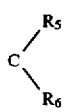

wherein $R_5$ and $R_6$ are each selected, independently of the other, from hydrogen, alkyl, cycloalkyl, cycloalkylalkyl, phenyl, and benzyl, it being understood that:
- the terms "alkenyl", and "alkoxy" denote straight-chain or branched groups having 1 to 6 carbon atoms inclusive which may be unsubstituted or substituted by one or more alkoxy,
- the term "aryl" denotes phenyl, naphthyl, or pyridyl,
- the radicals phenyl, benzyl, phenylalkyl, naphthyl, pyrimidyl, pyrimidyl, and benzhydryl may be unsubstituted or substituted by one or more halogen, hydroxy, alkyl, alkoxy, trifluoromethyl, or nitro,
- the term "cycloalkyl" denotes a ring system having 3 to 8 carbon atoms inclusive,
- the terms "cycloalkylalkyl", "arylalkyl", "phenylalkyl", and "naphthylalkyl" denote cycloalkyl, aryl, phenyl, or naphthyl bonded by way of a linear or branched carbon chain containing 1 to 6 carbon atoms inclusive, its possible geometric and/or optical isomers, in pure form or in the form of a mixture, and its pharmaceutically-acceptable addition salts with an acid or a base.

2. A compound according to claim 1, which is 5-benzoyl-1-methyl-1,3-dihydro-2H-pyrrolo[2,3-b]pyridin-2-one.

3. A method for treating a mammal afflicted with a condition requiring an analgesic comprising the step of administering to said mammal an analgesically effective amount of a compound of claim 1 which is effective for alleviation of said condition.

4. A pharmaceutical composition useful as an analgesic comprising an analgesically effective amount of a compound as claimed in claim 1, together with a pharmaceutically-acceptable excipient.

5. A pharmaceutical composition according to claim 4 wherein said composition additionally comprises caffeine.

6. A compound according to claim 1, which is 1,3-dihydro-1,3,3-trimethyl-5-acetyl-2H-Pyrrolo[2,3-b]pyridin-2-one.

7. A compound according to claim 1, which is 1,3-dihydro-1-methyl-5-acetyl-2H-pyrrolo[2,3-b]pyridin-2-one.

* * * * *

UNITED STATES PATENT AND TRADEMARK OFFICE
CERTIFICATE OF CORRECTION

PATENT NO. : 5,767,128
DATED : Jun. 16, 1998                                    Page 1 of 4
INVENTOR(S) : G. Guillaumet, M-C Viaud, L. Savelon,
P. Pavli, P. Renard, B. Pfeiffer,
D-H Caignard, J-G Bizot-Espiard It is certified that error appears in the above-indentified patent and that said Letters Patent is hereby corrected as shown below:

TITLE Page, [57] ABSTRACT: 3rd line below formula, insert a comma -- , -- after the word "base".

Column 4, line 63: "(IV) and (VII):" should read:
    -- (IV) and (VIII): --.

Column 6, line 20: In the formula, "$R_4$" should read:
    -- $R_3$ --.

Column 11, line 27: "$J_{3,2}$3.3 Hz);" should read:
    -- $J_{3,2}=3.3$ Hz); --.

Column 15, line 28: "1790 cm-1" should read:
    -- 1790 $cm^{-1}$ --.

Column 15, line 62: "1680 $cm^{31\ 1}$ (CO" should read:
    -- 1680 $cm^{-1}$ (CO --.

Column 16, line 23: "$J_2$5.9" should read: -- $J_2=5.9$ --.

Column 18, line 58: "(31H)-ONE" should read:
    --2(3H)-ONE --.

Column 21, line 66: "PYRIDIN-2(3-ONE" should read:
    -- PYRIDIN-2(3H)-ONE --.

Column 22, line 60: "(d,$H_7$,1H, $J_{5,7}$1.5 Hz);" should
    read -- (d,$H_7$,1H,$J_{5,7}=1.5$ Hz); --.

UNITED STATES PATENT AND TRADEMARK OFFICE
CERTIFICATE OF CORRECTION

PATENT NO. : 5,767,128
DATED : Jun. 16, 1998
INVENTOR(S) : G. Guillaumet, M-C Viaud, L. Savelon, P. Pavli, P. Renard, B. Pfeiffer, D-H Caignard, J-G Bizot-Espiard It is certified that error appears in the above-indentified patent and that said Letters Patent is hereby corrected as shown below:

Column 23, line 20: "(d,$H_5$,1H, $J_{5,7}$1.5 Hz)." should read:
-- (d,$H_5$,1H,$J_{5,7}$=1.5 Hz). --.

Column 23, line 52: "$J_2$7.4 Hz);" should read:
-- $J_2$=7.4 Hz); --.

Column 24, line 25: At the beginning of the line,
"oxazolo[b]" should read -- oxazolo[4.5-b] --.

Column 24, line 43: After "J-7.4 Hz);" insert -- 7.91 --

Column 24, line 45: At the beginning of the line,
"$H_5$1H," should read -- $H_5$,1H, --.

Column 28, line 5: "$H_{arom}$ 2H, J=8.8 Hz);" should read:
-- $H_{arom}$2H, J=8.8 Hz); --.

Column 28, line 39: At the beginning of the line,
"b]pyridin-2(3-one" should read:  -- b]pyridin-2(3H)-one --.

Column 28, line 64: "$J_2$4.8 Hz, $J_{32}$ 4.8 Hz);" should read:
-- $J_2$=4.8 Hz); --.

Column 29, line 8: "[4,5-b]pyridin-2(3H-one is" should
read -- [4,5-b]pyridin-2(3H)-one is --.

Column 29, line 66: "[4,5-b]pyridin-2(3H-one" should read
-- [4,5-b]pyridin-2(3H)-one --.

UNITED STATES PATENT AND TRADEMARK OFFICE
CERTIFICATE OF CORRECTION

PATENT NO. : 5,767,128
DATED : Jun. 16, 1998
INVENTOR(S) : G. Guillaumet, M-C Viaud, L. Savelon, P. Pavli, P. Renard, B. Pfeiffer, D-H Caignard, J-G Bizot-Espiard Page 3 Of 4

It is certified that error appears in the above-indentified patent and that said Letters Patent is hereby corrected as shown below:

Column 30, line 13: "(t, $CH_2$2H, J=7.4 Hz);" should read:
-- (t, $CH_2$,2H, J=7.4 Hz); --.

Column 31, line 14: At the beginning of the line,
"5-b]pyridin-2(3H-one" should read: -- 5-b]pyridin-2(3H)-one --.

Column 32, line 54: At the end of the line, "-2(3H-"
should read -- -2(3H)- --.

Column 35, line 31: "(5.57·10-4 mol)" should read:
-- (5.57 x 10-4 mol) --.

Column 35, line 52: In the middle of the line,
"3.79(s,2H,$CH_{CH2}$-N);" should read:
-- 3.79(s,2H,$CH_2$-N); --.

Column 35, line 54: "(s,1" should read -- (s,1H,$H_6$) --.

Column 38, line 52: "the terms "alkenyl"," should read
-- the terms "alkyl" "alkenyl", --.

UNITED STATES PATENT AND TRADEMARK OFFICE
CERTIFICATE OF CORRECTION

PATENT NO. : 5,767,128
DATED : Jun. 16, 1998
INVENTOR(S) : G. Guillaumet, M-C Viaud, L. Savelon, P. Pavli, P. Renard, B. Pfeiffer, D-H Caignard, J-G Bizot-Espiard It is certified that error appears in the above-indentified patent and that said Letters Patent is hereby corrected as shown below:

Column 38, line 58: First instance "pyrimidyl," should read -- pyridyl, --.

Signed and Sealed this

Thirteenth Day of April, 1999

Q. TODD DICKINSON

*Attest:*

*Attesting Officer*    Acting Commissioner of Patents and Trademarks